(12) United States Patent
Hagbard et al.

(10) Patent No.: US 11,713,448 B2
(45) Date of Patent: *Aug. 1, 2023

(54) METHODS FOR PRODUCING HEPATOCYTES

(71) Applicants: BioLamina AB, Sundyberg (SE); The University of Edinburgh, Edinburgh (GB)

(72) Inventors: Louise Kristina Hagbard, Sollentuna (SE); Carl Gunnar Jesper Ericsson, Hagersten (SE); Katherine Rachel Cameron, Edinburgh (GB); David Colin Hay, Midlothian (GB); Stuart John Forbes, East Lothian (GB); Hassan Rashidi, Edinburgh (GB)

(73) Assignee: BIOLAMINA AB, Sundyberg (SE)

( * ) Notice: Subject to any disclaimer, the term of this patent is extended or adjusted under 35 U.S.C. 154(b) by 461 days.

This patent is subject to a terminal disclaimer.

(21) Appl. No.: 16/902,368

(22) Filed: Jun. 16, 2020

(65) Prior Publication Data

US 2020/0308551 A1    Oct. 1, 2020

Related U.S. Application Data

(62) Division of application No. 15/338,352, filed on Oct. 29, 2016, now Pat. No. 10,683,486.

(60) Provisional application No. 62/248,389, filed on Oct. 30, 2015.

(51) Int. Cl.
| | |
|---|---|
| *C12N 5/00* | (2006.01) |
| *C12N 5/095* | (2010.01) |
| *C12N 5/074* | (2010.01) |
| *C12N 5/071* | (2010.01) |

(52) U.S. Cl.
CPC ............ *C12N 5/0695* (2013.01); *C12N 5/067* (2013.01); *C12N 5/0671* (2013.01); *C12N 5/0696* (2013.01); *C12N 2500/25* (2013.01); *C12N 2500/38* (2013.01); *C12N 2500/62* (2013.01); *C12N 2501/115* (2013.01); *C12N 2501/12* (2013.01); *C12N 2501/16* (2013.01); *C12N 2501/237* (2013.01); *C12N 2501/39* (2013.01); *C12N 2501/415* (2013.01); *C12N 2501/727* (2013.01); *C12N 2501/999* (2013.01); *C12N 2506/02* (2013.01); *C12N 2513/00* (2013.01); *C12N 2533/40* (2013.01); *C12N 2533/52* (2013.01); *C12N 2533/76* (2013.01); *C12N 2533/90* (2013.01)

(58) Field of Classification Search
None
See application file for complete search history.

(56) References Cited

U.S. PATENT DOCUMENTS

| | | |
|---|---|---|
| 2009/0170198 A1 | 7/2009 | Rezania et al. |
| 2010/0124781 A1 | 5/2010 | Nelson |
| 2013/0157368 A1 | 6/2013 | Buensuceso et al. |
| 2013/0330825 A1 | 12/2013 | Couture et al. |
| 2015/0164958 A1 | 6/2015 | Grinnemo et al. |
| 2018/0030415 A1 | 2/2018 | Nguyen et al. |

FOREIGN PATENT DOCUMENTS

| | | |
|---|---|---|
| CN | 103374546 A | 10/2013 |
| CN | 105647860 A | 6/2016 |
| CN | 106559994 A | 4/2017 |
| CN | 109789163 A | 5/2019 |
| EP | 2 457 998 A1 | 5/2012 |
| EP | 3 059 307 A1 | 8/2016 |
| WO | WO 2015/004539 A2 | 1/2015 |

OTHER PUBLICATIONS

Cameron et al.; Recombinant Laminins Drive the Differentiation and Self-Organization of hESC-Derived Hepatocytes; Stem Cell Reports; vol. 5; pp. 1250-1262; 2015.

Kikkawa et al.; Maintenance of hepatic differentiation by hepatocyte attachment peptides derived from laminin chains; Journal of Biomedical Materials Research; vol. 99A; Iss. 2; pp. 203-210; 2011.

Takayama et al.; Long-Term Self-Renewal of Human ES/iPS-Derived Hepatoblast-like Cells on Human Laminin III-Coated Dishes; Stem Cell Reports; vol. 1; pp. 322-335; 2013.

Amranul Haque et al., The effect of recombinant E-cadherin substratum on the differentiation of endoderm-derived hepatocyte-like cells from embryonic stem cells, Biomaterials, 2011, pp. 2032-2042, Elsevier.

Jason R. Spence et al., Directed differetiation of human pluripotent stem cells into intestinal tissue in vitro, Nature, Feb. 3, 2011, pp. 105-109.

*Primary Examiner* — Marcia S Noble
(74) *Attorney, Agent, or Firm* — Lippes Mathias LLP

(57) ABSTRACT

Methods for producing hepatocytes from pluripotent human stem cells are disclosed herein. The stem cells are plated on a cell culture substrate comprising two laminins. The stem cells are then exposed to different cell culture mediums to induce differentiation. The resulting hepatocytes have higher metabolic capacity compared to hepatocytes cultured on different substrates.

20 Claims, 28 Drawing Sheets

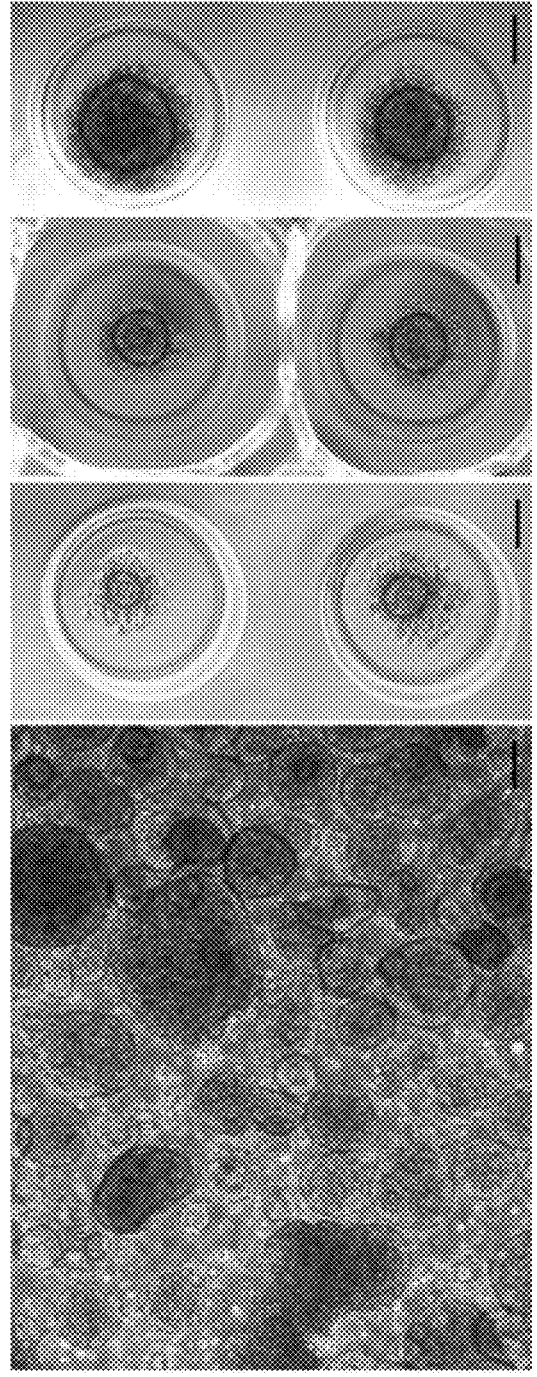
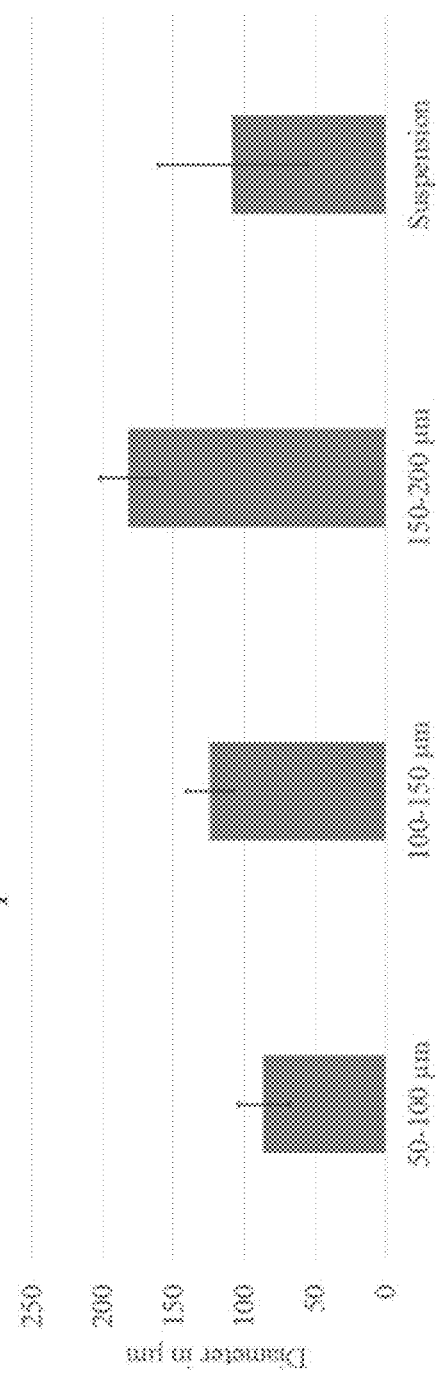

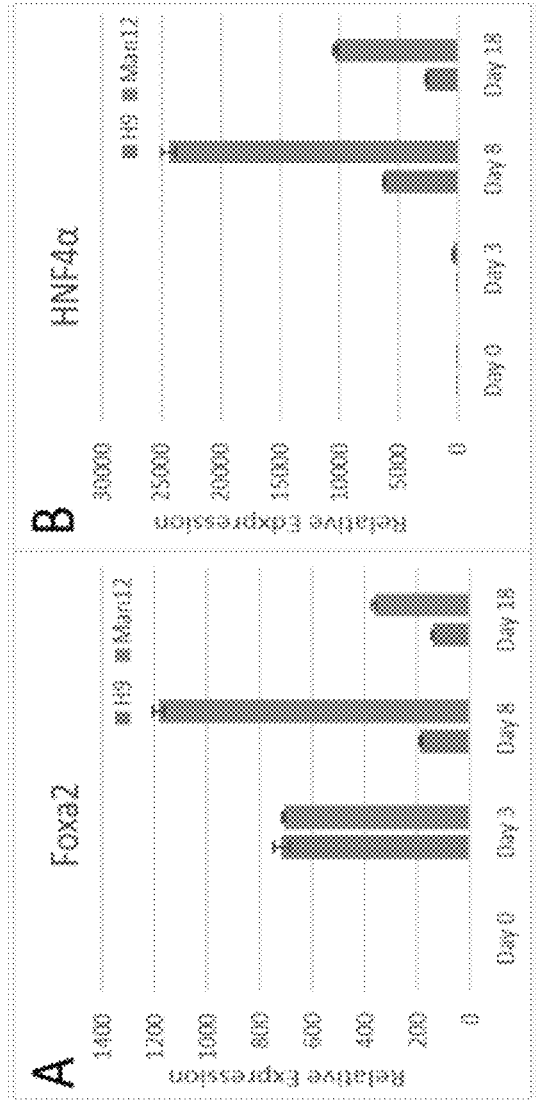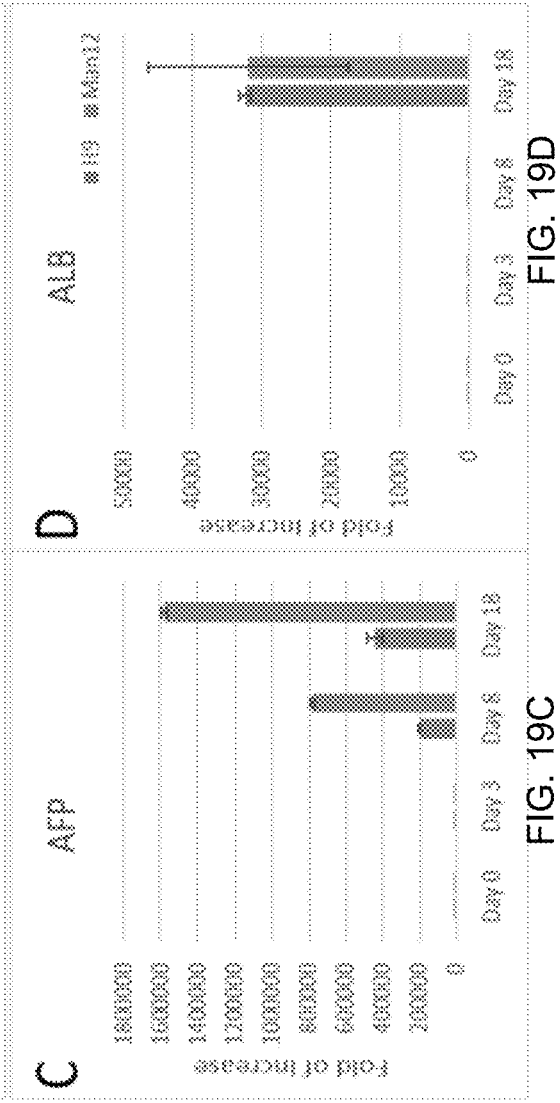
FIG. 19A, FIG. 19B, FIG. 19C, FIG. 19D

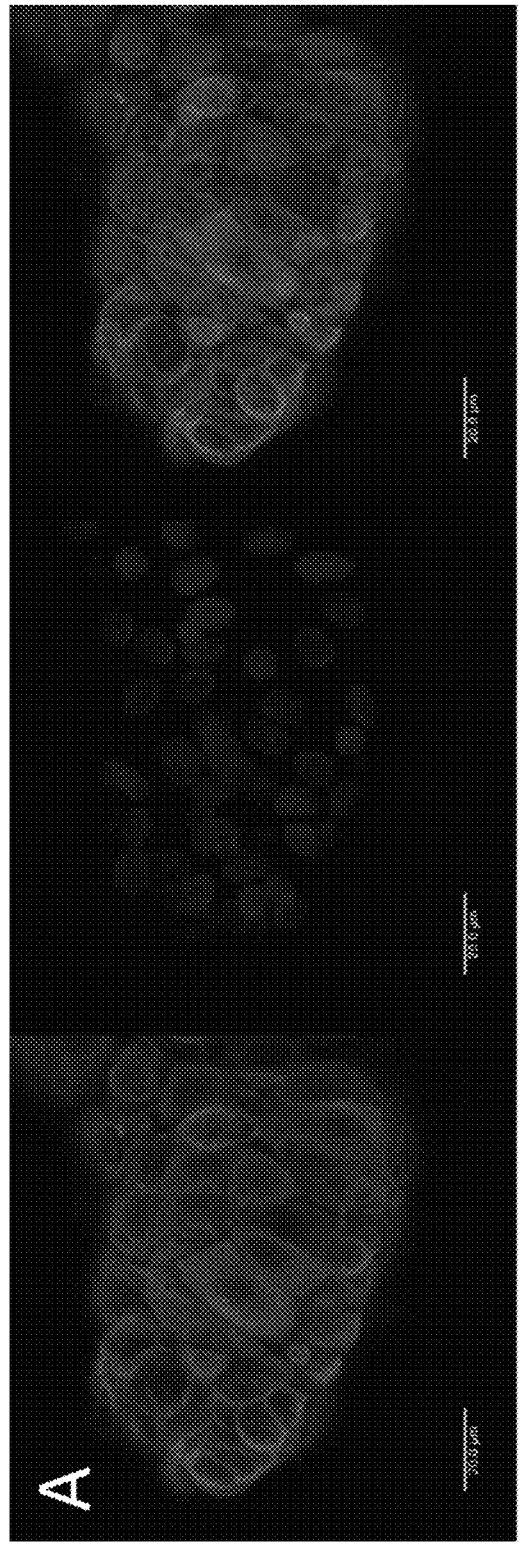
FIG. 23A. CYP3A
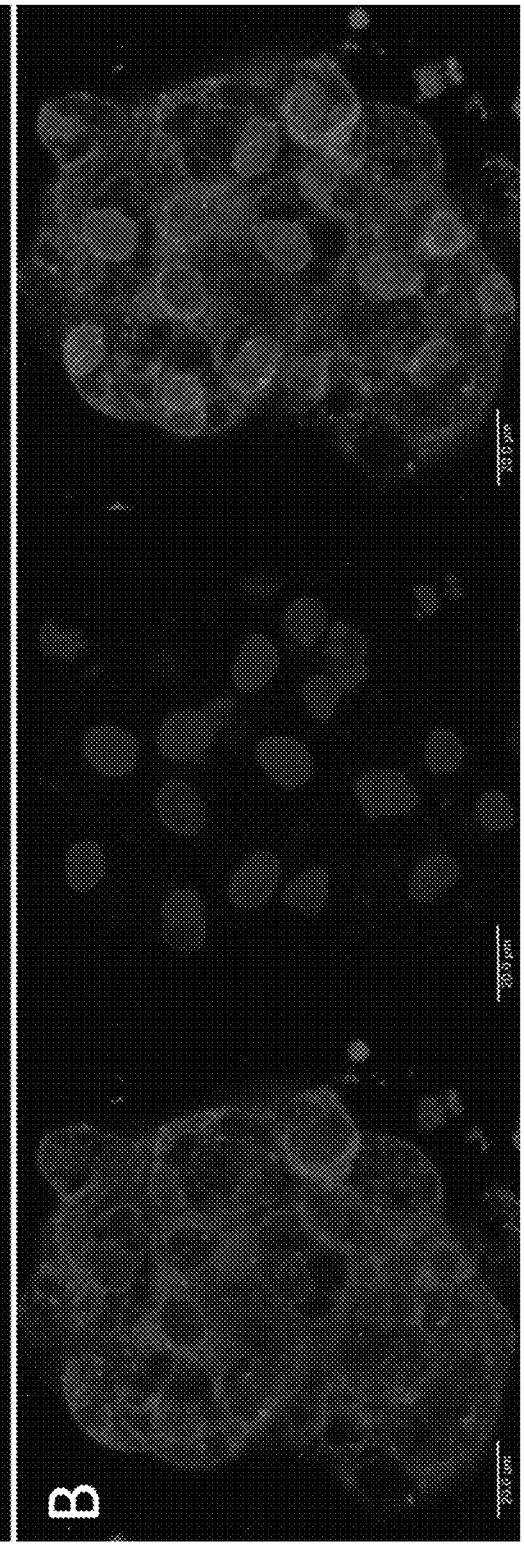
FIG. 23B. CYP2D6

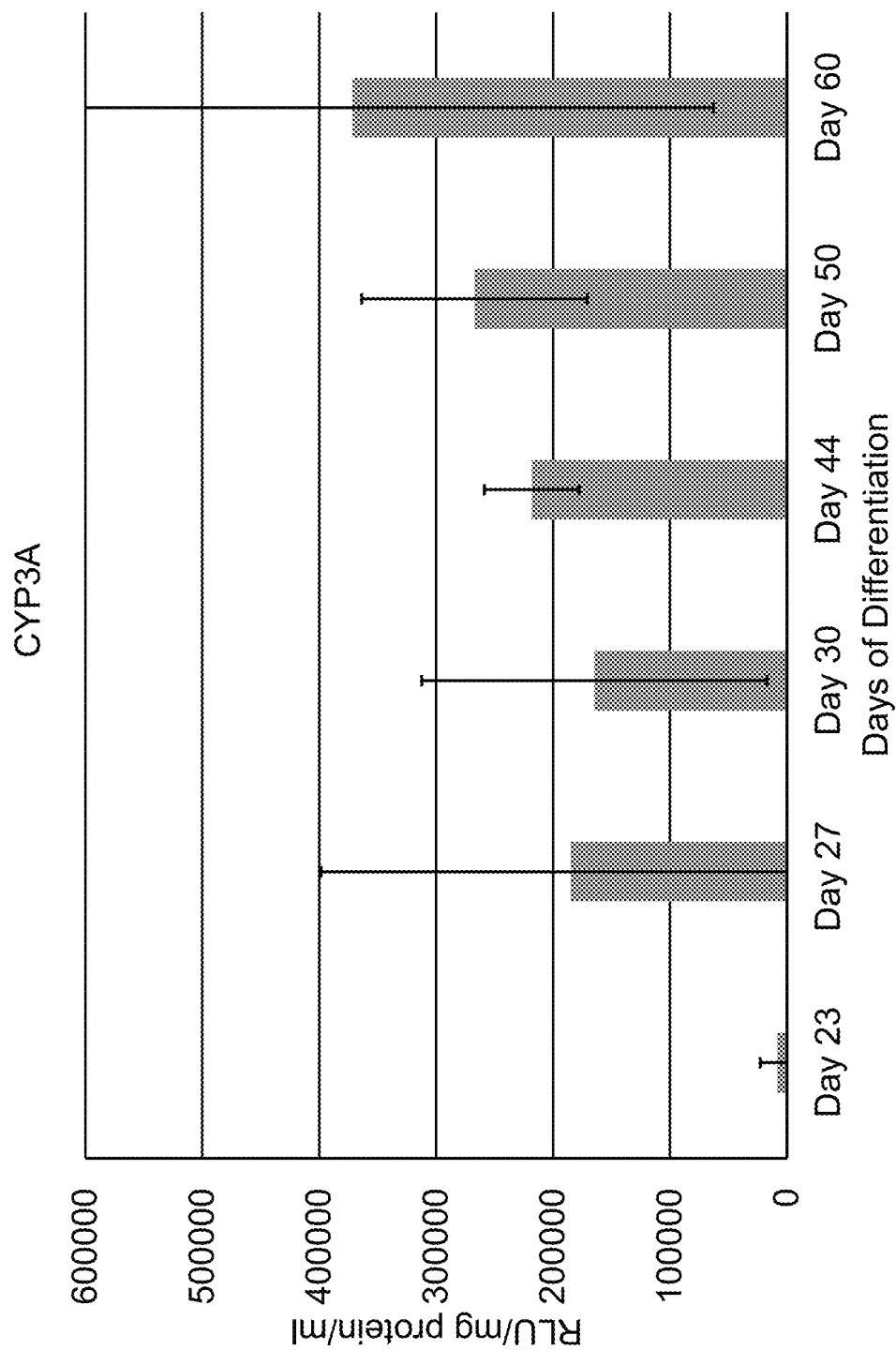

METHODS FOR PRODUCING HEPATOCYTES

CROSS-REFERENCE TO RELATED APPLICATIONS

This application is a divisional of U.S. patent application Ser. No. 15/338,352, filed on Oct. 29, 2016, now U.S. Pat. No. 10,683,486, which claims priority to U.S. Provisional Patent Application Ser. No. 62/248,389, filed on Oct. 30, 2015. The entirety of these applications is hereby incorporated by reference.

BACKGROUND

A stem cell is an undifferentiated cell from which specialized cells are subsequently derived. Pluripotent stem cells can be differentiated into any of the three germ layers: endoderm, mesoderm, or ectoderm. Post fertilization, pluripotent stem cells form every cell type in the human body, including less plastic stem cell populations such as adult stem cells, fetal stem cells, and amniotic stem cells. Embryonic stem cells are a type of pluripotent stem cell, and possess extensive self-renewal capacity and pluripotency. More recently another type of pluripotent stem cell, induced pluripotent stem cells, were produced from mammalian terminally differentiated cells by a process termed somatic cell reprogramming. The process by which a stem cell changes into a more specialized cell is referred to as differentiation, for example the differentiation of endodermal progenitor cells to hepatocytes.

Stem cell derived somatic cells represent a large source of cells for basic and translational science. While promising, there are many hurdles that need to be overcome to make this a reality. In particular, current protocols produce hepatocytes of variable function and longevity which is the product of using undefined components in the differentiation process. The use of Matrigel® and serum are prime examples, and remains a source of batch to batch variability in hepatocyte differentiation procedures. Matrigel® is a complex tumor and BM-like extract obtained from murine Engelbreth-Holm-Swarm (EHS) sarcoma tumor tissues. Matrigel® mainly contains murine LN-111, type IV collagen, perlecan and nidogen but also varying amounts of other materials, including growth factors and cellular proteins and, therefore, its composition is undefined and varies from batch-to-batch. More recent studies have used small molecules to replace growth factors, but while this dramatically drives down process costs, small molecules can have some off-target effects. Moreover those studies used Matrigel® and serum to drive the differentiation process, and by nature will therefore be variable. As a result, generating reliable, reproducible cultures of hepatocytes is difficult. Moreover, if these cells are to be used clinically, manufacturing processes must meet GMP guidelines. To comply with these guidelines, products containing animal derivatives are strictly controlled.

It would be desirable to develop methods that allow for differentiation of stem cells under chemically defined, xeno-free, pathogen-free, and stable batch-to-batch conditions into differentiated cells, particularly hepatocytes. Desirably, such methods should provide large quantities of such differentiated cells from GMP grade human embryonic stem cells (hESCs).

BRIEF DESCRIPTION

Disclosed herein are methods for producing hepatocytes with more natural properties and more differentiated function. Generally, those methods comprise: plating pluripotent human stem cells on a cell culture substrate comprising (i) a first laminin which is laminin-521 and (ii) a second laminin selected from the group consisting of laminin-111 and laminin-221, wherein the laminin-521 and the second laminin are each either an intact protein or a protein fragment; and culturing the pluripotent human stem cells to obtain the hepatocytes. The resulting hepatocytes exhibit efficient hepatocyte specification, organisation, maturation and significant improvements in cell function and stability. It is believed that the laminins suppress inappropriate gene regulatory networks controlling cell proliferation, stem cell self-renewal, and colon and fibroblast specification. The stem cells themselves should be research and GMP grade.

The weight ratio of the laminin-521 to the second laminin may be from about 1:4 to about 1:1. In other words, there is more of the second laminin compared to the laminin-521.

The culturing of the pluripotent human stem cells may be performed by: (a) culturing the cells in an endoderm differentiation medium containing activin A and Wnt3a; (b) culturing the cells in a hepatoblast differentiation medium; and (c) then culturing the cells in a hepatocyte maturation medium containing hydrocortisone (HC), hepatocyte growth factor (HGF) and oncostatin m (OSM).

The cells may be cultured in the endoderm differentiation medium for a period of about 60 hours to about 84 hours. The cells may be cultured in the hepatoblast differentiation medium for a period of about 73 hours to about 180 hours. The cells may be cultured in the hepatocyte maturation medium for at least 216 hours.

The endoderm differentiation medium may include RMPI 1640 and B27. The activin A in the endoderm differentiation medium may be present in an amount of about 50 ng/mL to about 150 ng/mL. The Wnt3a in the endoderm differentiation medium may be present in an amount of about 20 ng/mL to about 100 ng/mL.

The hepatoblast differentiation medium may be made from KO-DMEM, 20% Serum Replacement, 1% non-essential amino acids, 0.1 mM beta-mercaptoethanol, and 1% dimethyl sulfoxide. The hepatocyte growth factor in the hepatocyte maturation medium may be present in an amount of about 5 ng/mL to about 20 ng/mL. The oncostatin m in the hepatocyte maturation medium may be present in an amount of about 10 ng/mL to about 30 ng/mL.

Alternatively, the culturing of the pluripotent human stem cells could be performed according to the Avior procedure or the Cameron procedure.

The resulting hepatocytes may exhibit CYP1A2 activity of at least 600,000 RLU/mg/mL. Alternatively, the resulting hepatocytes may exhibit CYP3A activity of at least 800,000 RLU/mg/mL.

Sometimes, the cell culture substrate further comprises a cadherin. The cadherin can be e-cadherin. The weight ratio of (the first laminin+the second laminin) to the cadherin may be from about 5:1 to about 15:1.

Generally, the cell culture substrate does not contain any differentiation inhibitors, feeder cells, differentiation inductors, or apoptosis inhibitors.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

FIGS. 18A-18E are pictures showing three-dimensional spheroids of human embryonic stem cells (hESCs) cultured to form hepatocyte-like cells. FIG. 18A is a picture of spheroids of random size formed in poly(hydroxyethyl methyl methacrylate). FIG. 18B is a picture of spheroids of size 50 μm to 100 μm formed in agarose. FIG. 18C is a picture of spheroids of size 100 μm to 150 μm formed in agarose. FIG. 18D is a picture of spheroids of size 150 μm to 200 μm formed in agarose. FIG. 18E is a bar graph showing the range of hepatosphere sizes created. The y-axis is in micrometers (μm), and runs from 0 to 250 at intervals of 50.

FIGS. 19A-19D are graphs showing hepatic gene expression in hepatospheres.

FIG. 19A is a bar graph showing relative expression over time of the Foxa2 gene. The y-axis runs from 0 to 1400 at intervals of 200. The x-axis is, running from left to right, day 0, day 3, day 8, and day 18. For each day, the left bar is H9 cell line, and the right bar is Man12 cell line.

FIG. 19B is a bar graph showing relative expression over time of the HNF4a gene. The y-axis runs from 0 to 30000 at intervals of 5000. The x-axis is, running from left to right, day 0, day 3, day 8, and day 18. For each day, the left bar is H9 cell line, and the right bar is Man12 cell line.

FIG. 19C is a bar graph showing the fold of increase in expression of alpha fetoprotein (AFP) over time. The y-axis runs from 0 to 1,800,000 at intervals of 200,000. The x-axis is, running from left to right, day 0, day 3, day 8, and day 18. For each day, the left bar is H9 cell line, and the right bar is Man12 cell line.

FIG. 19D is a bar graph showing the fold of increase in expression of albumin (ALB) over time. The y-axis runs from 0 to 50,000 at intervals of 10,000. The x-axis is, running from left to right, day 0, day 3, day 8, and day 18. For each day, the left bar is H9 cell line, and the right bar is Man12 cell line.

FIG. 23A is a set of three pictures taken on day 18 showing CYP3A produced in three-dimensional hepatospheres. The line at the bottom left of each stain indicates 20 μm.

FIG. 23B is a set of three pictures taken on day 18 showing CYP2D6 produced in three-dimensional hepatospheres. The line at the bottom left of each stain indicates 20 μm.

FIG. 23C is a bar graph showing CYP3A function over time. The y-axis is RLU/mg protein/ml, and runs from 0 to 600,000 at intervals of 100,000. The x-axis is, running from left to right, day 23, day 27, day 30, day 44, day 50, and day 60.

DETAILED DESCRIPTION

Figure 1:
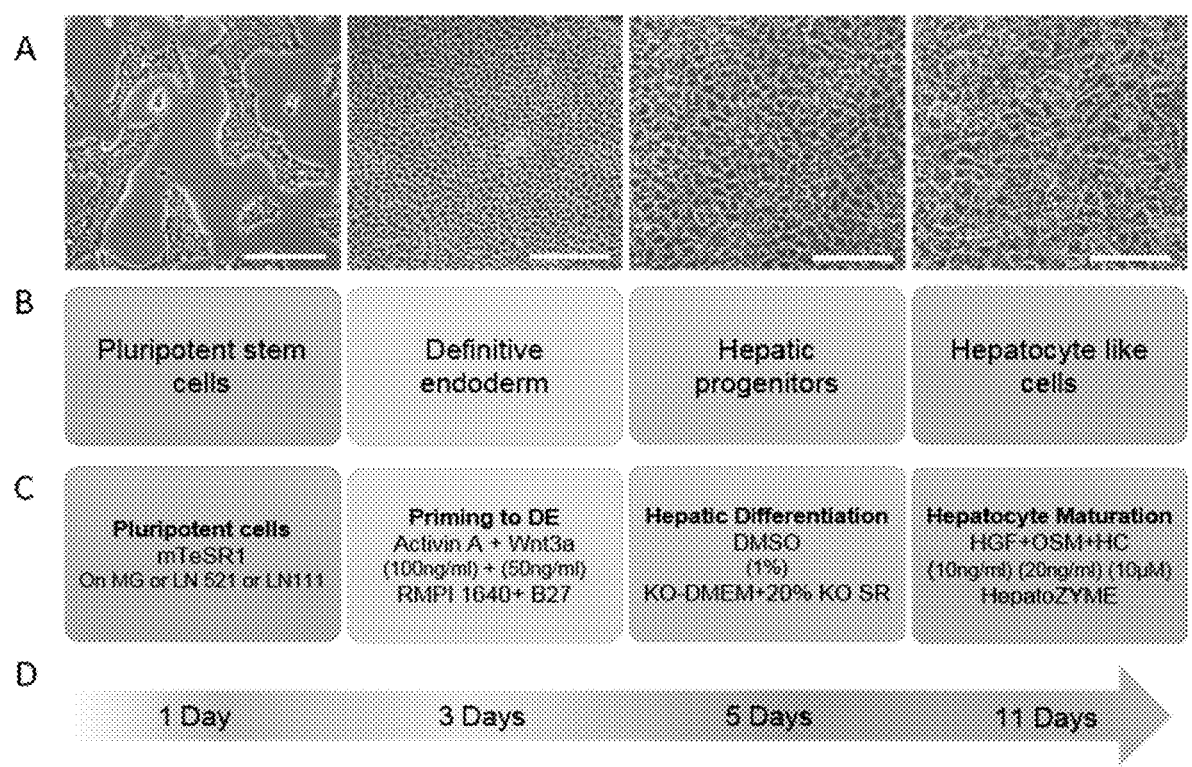
FIG. 1 is a representation of a differentiation protocol, including phase contrast images of representative fields of view, cell types present at each differentiation stage, growth factors/molecules and media used, and the time line for each stage.

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

All publications, patents, and patent applications discussed herein are hereby incorporated by reference in their entirety.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

Several well-known references that may be relevant to the present disclosure include: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, Second Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), or the Ambion 1998 Catalog (Ambion, Austin, Tex.).

As used herein, the term "laminin-521" refers to the protein formed by joining α5, β2 and γ1 chains together. The term should be construed as encompassing both recombinant laminin-521 and heterotrimeric laminin-521 from naturally occurring sources.

As used herein, the term "laminin-111" refers to the protein formed by joining α1, β1 and γ1 chains together. The term should be construed as encompassing both recombinant laminin-111 and heterotrimeric laminin-111 from naturally occurring sources.

As used herein, the term "laminin-221" refers to the protein formed by joining α2, β2 and γ1 chains together. The term should be construed as encompassing both recombinant laminin-221 and heterotrimeric laminin-221 from naturally occurring sources.

The term "intact" refers to the protein being composed of all of the domains of the α-chain, β-chain, and γ-chain, with the three chains being joined together to form the heterotrimeric structure. The protein is not broken down into separate chains, fragments, or functional domains. The term "chain" refers to the entirety of the alpha, beta, or gamma chain of the laminin protein. The term "fragment" refers to any protein fragment which contains one, two, or three functional domains that possesses binding activity to another molecule or receptor. However, a chain should not be considered a fragment because each chain possesses more than three such domains. Similarly, an intact laminin protein should not be considered a fragment. Examples of functional domains include Domains I, II, III, IV, V, VI, and the G domain.

Laminins are a family of heterotrimeric glycoproteins that reside primarily in the basal lamina. They function via binding interactions with neighboring cell receptors on the one side, and by binding to other laminin molecules or other matrix proteins such as collagens, nidogens or proteoglycans. The laminin molecules are also important signaling molecules that can strongly influence cellular behavior and function. Laminins are important in both maintaining cell/tissue phenotype, as well as in promoting cell growth and differentiation in tissue repair and development.

Laminins are large, multi-domain proteins, with a common structural organization. The laminin molecule integrates various matrix and cell interactive functions into one molecule. A laminin protein molecule comprises one α-chain subunit, one β-chain subunit, and one γ-chain subunit, all joined together in a trimer through a coiled-coil domain. The twelve known laminin subunit chains can form at least 15 trimeric laminin types in native tissues. Within the trimeric laminin structures are identifiable domains that possess binding activity towards other laminin and basal lamina molecules, and membrane-bound receptors. For example, domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

There exist five different alpha chains, three beta chains and three gamma chains that in human tissues have been found in at least fifteen different combinations. These molecules are termed laminin-1 to laminin-15 based on their historical discovery, but an alternative nomenclature describes the isoforms based on their chain composition, e.g. laminin-111 (laminin-1) that contains alpha-1, beta-1 and gamma-1 chains. Four structurally defined family groups of laminins have been identified. The first group of five identified laminin molecules all share the β1 and γ1 chains, and vary by their α-chain composition (α1 to α5 chain). The second group of five identified laminin molecules, including laminin-521, all share the β2 and γ1 chain, and again vary by their α-chain composition. The third group of identified laminin molecules has one identified member, laminin-332, with a chain composition of α3β3γ2. The fourth group of identified laminin molecules has one identified member, laminin-213, with the newly identified γ3 chain (α2β1γ3).

The present disclosure relates to more efficient methods of culturing stem cells to obtain differentiated hepatocytes that behave more like primary hepatocytes. In particular, the stem cells are cultured on a substrate that contains laminin-521 and a second laminin selected from laminin-111 and laminin-221. This results in more differentiated hepatocytes with more natural behavior than cells grown on substrates containing an undefined and alternative blend of extracellular matrices.

Differentiated cells typically require two things to survive and reproduce: (1) a substrate or coating that provides a structural support for the cell; and (2) a cell culture medium to provide nutrition to the cell. The substrate or coating (1) is typically formed as a layer in a container, for example a petri dish or in the well of a multi-well plate. Application of different cell culture mediums at appropriate time intervals in combination with the substrates containing two laminins result in mature hepatocytes with more natural functions/properties.

The stem cells that can be used with the methods and materials disclosed herein are pluripotent human stem cells. Such stem cells can include induced pluripotent stem cells, embryonic stem cells, adult stem cells, fetal stem cells, amniotic stem cells, and generally any pluripotent stem cell.

Initially, the stem cells are plated on a cell culture substrate. The substrate contains two laminins. The first laminin is laminin-521 (LN-521). The second laminin is either laminin-111 (LN-111) or laminin-221 (LN-221). Each laminin can be an intact protein or a protein fragment, although in preferred embodiments the laminins are intact proteins.

The stem cells can be plated on the surface of the cell culture substrate to obtain conventional monolayer cultures (i.e. two-dimensional or 2D). In some alternative embodiments, after plating on the laminin-containing cell culture substrate, the stem cells can be suspended and replated to obtain three-dimensional structures (3D). 3D spheroids can be obtained, for example, using suspension methods or by using a microplate platform that permits control of spheroid size. For example, substrates such as poly(hydroxyethyl methyl methacrylate) (poly-HEMA) or agarose can be used to form the 3D spheroids. The agarose, for example, contains micro wells that control the size to which the aggregate can grow. Other 3D cultivation technologies are known in the art. Suspension culture on low adherence plates can generate a heterogeneous population of aggregates with varying sizes, for example 50 µm to 500 µm.

In particular embodiments, it is contemplated that the weight ratio of the laminin-521 to the laminin-111/211 in the substrate is from about 1:4 to about 1:2, including from about 1:4 to about 1:1 (i.e. less laminin-521 than the laminin-111/211). In particular, laminin-521 and laminin-111 activate α6β1 integrins, which in turn leads to activation of the PI3K/Akt pathway. This increases the pluripotency, self-renewal, and/or proliferation of the differentiated hepatocytes. Many different molecules can activate the PI3K/Akt pathway, though with different efficiencies. For example, TGF beta 1 and bFGF activate this pathway. The use of laminin-521 or laminin-111 allows the quantity of such molecules to be reduced in the cell culture medium. The use of laminin-521 and laminin-511 also allows for single-cell suspension passaging without the addition of cell-detrimental rho-kinase (ROCK) inhibitor to increase cell survival after single-cell enzymatic dissociation.

In some embodiments, the cell culture substrate may also comprise a cadherin. Cadherins are a class of type-1 transmembrane proteins that play important roles in cell adhesion, ensuring that cells within tissues are bound together. They are dependent on calcium ($Ca^{2+}$) ions to function. Cadherins are also known as desmogleins and desmocollins. Structurally, cadherins contain extracellular $Ca^{2+}$-binding domains. In particular embodiments, the cadherin used in the cell culture substrate is epithelial cadherin or e-cadherin. The weight ratio of the two laminins to the cadherin may be from about 5:1 to about 15:1, or from about 5:1 to about 10:1.

The cell culture substrate is used in combination with multiple cell culture mediums to obtain the desired hepatocytes. Four different cell culture mediums are used, which are described below and referred to herein as mTeSR1, endoderm differentiation medium, hepatoblast differentiation medium, and hepatocyte maturation medium.

The mTeSR1 medium is prepared as described in (Ludwig, T. E., Bergendahl, V., Levenstein, M. E., Yu, J., Probasco M. D. and Thomsom, J. A. (2006); Feeder-independent culture of human embryonic stem cells; Nat Methods 8, 637-646) with several exceptions. First, recombinant human FGF basic (R@DSystems) is used instead of zbFGF. Secondly, Insulin-Transferrin-Selenium Supplement (Invitrogen) added in already made medium was used as a source of the elements instead of the method described in the article. This is commercially available from Stem Cell Technologies (catalog no. 05857).

The endoderm differentiation medium includes RMPI 1640 (Life Technologies catalog no. 11875-093) and 1×B27. B27 supplement without vitamin A can be obtained from Life Technologies (catalog no. 12587-010). Activin A (Peprotech, catalog no. 120-14E) is present in the endoderm differentiation medium in an amount of about 50 ng/mL to about 150 ng/mL, including about 100 ng/mL. Wnt3a (R&D, catalog no. 1324-WN/CF) is present in the endoderm differentiation medium in an amount of about 20 ng/mL to about 80 ng/mL, including about 50 ng/mL.

The hepatoblast differentiation medium is made of 77.5 vol % KO-DMEM (Life Technologies catalog no. 10829-018), 20 vol % Serum Replacement (Life Technologies catalog no. 10828-028), 0.5 vol % Glutamax (Life Technologies catalog no. 35050-038) 1 vol % non-essential amino acids (Life Technologies catalog no. 11140-035), 0.1 mM beta-mercaptoethanol (Life Technologies catalog no. 31350-010), and 1 vol % dimethyl sulfoxide (Life Technologies catalog no. d5879).

The hepatocyte maturation medium made of HepatoZYME™ medium (Life Technologies catalog no. 17705-021), containing 1% Glutamax (Life Technologies catalog no. 35050-038). Hepatocyte growth factor (Peprotech, catalog no. 100-39) is present in the hepatocyte maturation medium in an amount of about 5 ng/mL to about 20 ng/mL, including about 10 ng/mL Oncostatin m (Peprotech, catalog no. 300-10) is also present in the hepatocyte maturation medium, in an amount of about 10 ng/mL to about 30 ng/mL, including about 20 ng/mL. Finally, hydrocortisone is present in the hepatocyte maturation medium at a concentration of about 5 micromolar (µM) to about 20 µM, including about 10 µM.

Returning to FIG. 1, the stem cells are first plated onto the cell culture substrate made up of two laminins as described above, and fed with the mTeSR1 medium for about 1 day to about 3 days. If 3D cell structures are desired, then the stem cells are replated to obtain the 3D cell structures. Differentiation is then initiated by removing the mTeSR1 medium and applying the endoderm differentiation medium to the plated stem cells (2D or 3D). The cells are cultured in the endoderm differentiation medium for a period of about 60 hours to about 84 hours, including about 72 hours (i.e. three days). The medium may be periodically changed, for example every 24 hours.

Next, the endoderm differentiation medium is removed, and the hepatoblast differentiation medium is applied to the plated stem cells. The cells are cultured in the hepatoblast differentiation medium for a period of about 108 hours to about 132 hours, including about 120 hours (i.e. five days). The medium may be periodically changed, for example every 48 hours.

Next, the hepatoblast differentiation medium is removed, and the hepatoblast maturation medium is applied to the plated stem cells (2D or 3D). The cells are cultured in the hepatoblast maturation medium for a period of at least 144 hours (i.e. six days). The medium may be periodically changed, for example every 24 hours. This results in a total time period of about 14 days of differentiation and maturation of the stem cells, which differentiate into hepatocytes.

Alternatively, the stem cells are cultured according to the Avior procedure. The Avior procedure uses an endoderm differentiation medium, a hepatic specification medium, a hepatic differentiation medium, and a hepatic maturation medium. The following table identifies all of the ingredients used in each medium in the Avior procedure:

| Medium | Ingredient | cat no. | Source | Volume | Final Conc. |
| --- | --- | --- | --- | --- | --- |
| Endoderm differentiation | RPMI 1640 | 11875-093 | Life Technologies | 500 mL | |
| | B27 | 12587-010 | Life Technologies | 10 mL | 0.5% |
| | Penicillin-Streptomycin | 03-031-1C | Biological Industries | 5 mL | 1% |

-continued

| Medium | Ingredient | cat no. | Source | Volume | Final Conc. |
|---|---|---|---|---|---|
| | Activin A | 338-AC | R&D | 1 μL/mL | 100 ng/ml |
| | Wnt3a | 5036-WN-010 | R&D | 5 μL/mL | 50 ng/ml |
| | Hepatocyte growth factor | 100-39 | Peprotech | 0.5 μL/mL | 10 ng/mL |
| hepatic specification | KO DMEM | 10829-018 | Life Technologies | 400 mL | |
| | KO-SR | 10828-028 | Life Technologies | 100 mL | 20% |
| | L-Alanyl-L-Glutamin (Glutamax) | 030221B | Biological Industries | 2.5 mL | 1% |
| | Non Essential Amino Acids (NEAA) | 01-340-1B | Biological Industries | 5 mL | 1% |
| | Dimethyl sulfoxide | D4540 | Life Technologies | 5 mL | 1% |
| | beta mecaptoethanol | M6250 | Life Technologies | 3.33 mL | 0.33 mM |
| | Penicillin-Streptomycin | 03-031-1C | Biological Industries | 5 mL | 1% |
| hepatic differentiation | Iscove's Modified Dulbecco's Media (IMDM) | 01-058-1A | Biological Industries | | |
| | Penicillin-Streptomycin | 03-031-1C | Biological Industries | 5 mL | 1% |
| | Insulin-Transferrin-Selenium | I3146 | Sigma | 0.5 mL | |
| | Dexmethasone | D4902 | Sigma | 0.5 μL/mL | 0.5 μM |
| | oncostatin M | 300-10 | Peprotech | 1 μL/mL | 20 ng/mL |
| | basic fibroblast growth factor | | | 2 μL/mL | 4 ng/mL |
| hepatic maturation | RPMI-1640 (powder) | R6504 | Sigma | | |
| | sodium bicarbonate | S5761 | Sigma | | |
| | Insulin-Transferrin-Selenium + 3 | I2771 | Sigma | 5 mL | 0.10% |
| | Lithocholic acid | L6250 | Sigma | 1 μL/mL | 10 μM |
| | Vitamin K (MK-4) | V9378 | Sigma | 1 μL/mL | 10 μM |
| | Hepatocyte growth factor | 100-39 | Peprotech | 1 μL/mL | 10 ng/mL |
| | Penicillin-Streptomycin | 03-031-1C | Biological Industries | 5 mL | 1% |
| | Dexmethasone | D4902 | Sigma | 0.5 μL/mL | 0.5 μM |

In the Avior procedure, the pluripotent stem cells are cultured in a humidified incubator at 37° C. and 5% $CO_2$ until the cells reach 50% confluence. Again, the stem cells can have a two-dimensional (2D) or three-dimensional (3D) structure prior to differentiation. Differentiation is initiated by exposing the stem cells to the endoderm differentiation medium for 72 hours, replacing with fresh media every 24 hours. After 72 hours, the cells are exposed to the hepatic specification medium for 4 days, replacing with fresh media every 24 hours. Next, the cells are exposed to the hepatic differentiation medium for 5 days, replacing with fresh media every 24 hours. Finally, the cells are exposed to the hepatic maturation medium for 4 days, replacing with fresh media every 24 hours, for a total of 16 days.

As another alternative, the stem cells are cultured according to the Cameron procedure. The Cameron procedure uses an endoderm differentiation medium, a hepatoblast differentiation medium, and a hepatocyte maturation medium that is very similar to the three mediums described above. The following table identifies all of the ingredients used in each medium in the Cameron procedure:

| Medium | Ingredient | cat no. | Source | Volume | Final Conc. |
|---|---|---|---|---|---|
| endoderm differentiation | RPMI 1640 | 11875-093 | Life Technologies | 500 mL | |
| | B27 | 12587-010 | Life Technologies | 10 mL | 0.5% |
| | Penicillin-Streptomycin | 15140-122 | Life Technologies | 5 mL | 1% |
| | Activin A | 120-14E | Peprotech | 1 μL/mL | 100 ng/ml |
| | Wnt3a | 1324-WN/CF | R&D | 5 μL/mL | 50 ng/ml |
| hepatoblast differentiation | KO DMEM | 10829-018 | Life Technologies | 400 mL | |
| | KO-SR | 10828-028 | Life Technologies | 100 mL | 20% |
| | GlutaMAX-I | 35050-038 | Life Technologies | 2.5 mL | 1% |

-continued

| Medium | Ingredient | cat no. | Source | Volume | Final Conc. |
|---|---|---|---|---|---|
| | Minimal essential medium Non-Essential Amino Acids | 11140-035 | Life Technologies | 5 mL | 1% |
| | Dimethyl sulfoxide | D5879 | Life Technologies | 5 mL | 1% |
| | beta mercaptoethanol | 31350-010 | Life Technologies | 1 mL | 0.1 mM |
| hepatic maturation | HepatoZYME-SFM | 17705-021 | Life Technolgies | 500 mL | |
| | GlutaMAX-I | 35050-038 | Life Technologies | 2.5 mL | 1% |
| | hydrocortisone- 21 hemisuccinate sodium salt | H4881-1G | Sigma | 5 mL | 10 µM |
| | Hepatocyte growth factor | 100-39 | Peprotech | 1 µL/mL | 20 ng/mL |
| | oncostatin M | 300-10 | Peprotech | 1 µL/mL | 10 ng/mL |
| | Penicillin-Streptomycin | 15140-122 | Life Technologies | 5 mL | 1% |

In the Cameron procedure, the pluripotent stem cells are cultured in a humidified incubator at 37° C. and 5% $CO_2$ until the cells reach 20 to 30% confluence. Again, the stem cells can have a two-dimensional (2D) or three-dimensional (3D) structure prior to differentiation. Differentiation is initiated by replacing culture medium with the endoderm differentiation medium. The media is replaced with fresh media every 24 hours for a period of 72 hours. After 72 hours, the media is replaced with the hepatocyte differentiation medium for 5 days, replacing every 48 hours. After 5 days, the media is replaced with the hepatocyte maturation medium, changing every 48 hours until day 20. The cells gradually exhibit morphological changes from a spiky and triangular shape to a characteristic liver morphology displaying a polygonal appearance.

After about 14 days, the identity of the cells (i.e. that they have differentiated into hepatocytes) can be verified by expression of markers including CYP3A4, CYP1A2, Oct4, Nanog, albumin, alpha fetoprotein (AFP), FOXA2, HNF4A, SOX17, CK19, and CYP2D6. The hepatocytes are then ready for use in desired applications.

The cell culture systems formed by the cell culture substrate and the various cell culture mediums work extremely well for producing hepatocytes from stem cells in a completely defined environment and xeno-free conditions without feeders or any inhibitors of apoptosis. It is noted that hepatocytes produced by the Cameron procedure are generally more stable than those produced by the Avior procedure, in that they possess Cytochrome P450 1A2 and 3A activity for a longer time period (10 days vs 1-2 days). It is contemplated that the cell culture system will be completely defined and xeno-free. The system (i.e. both the substrate and any cell culture mediums) should also be devoid of any differentiation inhibitors, feeder cells, or differentiation inductors, or apoptosis inhibitors. Examples of feeder cells include mouse fibroblasts or human foreskin fibroblasts. Examples of differentiation inductors include Noggin or keratinocyte growth factor.

The following examples are for purposes of further illustrating the present disclosure. The examples are merely illustrative and are not intended to limit devices made in accordance with the disclosure to the materials, conditions, or process parameters set forth therein.

EXAMPLES

Example 1

Cell Culture

H9 human embryonic stem cells (hESCs) were cultured and maintained in a humidified 37° C., 5% $CO_2$ incubator. Three different substrates were then prepared in 96-well plates. The first substrate was pre-coated with Matrigel® (MG), and served as a control. The second substrate was coated with 5 micrograms per square centimeter ($\mu g/cm^2$) of laminin-521 (LN-521). The third substrate was coated with 5 $\mu g/cm^2$ of a blend of laminin-521 and laminin-111 at a 1:3 weight ratio (Biolamina, Sweden) (abbreviated here as LN-111).

Differentiation was initiated at 40% confluence, by replacing serum-free medium mTESR1 (Stem Cell Technologies) with endoderm differentiation medium-RPMI 1640 containing 1×B27 (Life Technologies), 100 ng/mL Activin A (PeproTech) and 50 ng/mL Wnt3a (R&D). The medium was changed every 24 hours, for 72 hours. On day 4, endoderm differentiation medium was replaced with hepatoblast differentiation medium, and this was renewed every second day for a further five days. The medium consisted of KO-DMEM (Life Technologies), Serum Replacement (Life Technologies), 0.5% Glutamax (Life Technologies), 1% non-essential amino acids (Life Technologies), 0.2% β-mercaptoethanol (Life Technologies) and 1% dimethyl sulfoxide (Sigma) for 5 days. At Day 9, differentiating cells were cultured in hepatocyte maturation medium HepatoZYME (Life Technologies) containing 1% Glutamax (Life Technologies), supplemented with 10 ng/mL hepatocyte growth factor (Peprotech) and 20 ng/mL oncostatin m (Peprotech).

Cryoplateable human hepatocytes were plated and maintained according to the instructions of vendor Life Technologies. Briefly, cryoplateable hepatocytes were resuscitated in thawing medium (Life Technologies, catalog no. CM3000) and plated onto the pre-coated 96 well plates. Cells-attached to all matrices efficiently and were maintained in an incubator set at 37 degrees Celsius and $CO_2$ levels set to 5%. At 24 hours post-plating, the medium was changed to an incubation medium (catalog no. CM4000).

FIG. 1 contains four rows illustrating the differentiation protocol. The uppermost row A contains a set of phase contrast images providing representative views of the cells during each stage. Row B lists the cell type present at each differentiation stage (i.e., pluripotent stem cells, definitive endoderm, hepatic progenitors, and hepatocyte like cells). Row C lists the growth factors/molecules and media used at each stage of the protocol. Row D indicates the time for each stage of the differentiation protocol. The last stage, hepatocyte maturation, can extend beyond day 11.

Methods

Total RNA was isolated from cells using Trizol reagent. RNA quantification and quality was assessed using a Nanodrop system. The Life Technologies Superscript III reverse transcription kit was employed to prepare the cDNA. Quantitative PCR was performed with Taqman Fast Advance Mastermix and the appropriate primer pair and analysed using a Roche LightCycler 480 Real-Time PCR System. Gene expression was normalized to glyceraldehyde 3-phosphate dehydrogenase (GAPDH) and expressed as relative expression over the control sample (hESC on Day 0 of differentiation). Quantitative PCRs were performed in triplicate. Data analysis was performed using Roche LightCycler 480 Software (version 1.5). Levels of significance were measured by the statistical function student t-test, wherein significant values are those with a p-value less than 0.05.

Immunocytochemistry analysis was subsequently performed on hESC-derived hepatocytes. Cell cultures were fixed in 100% ice-cold methanol at −20 degrees Celsius for 30 minutes, and adjacent cells were pre-washed twice with PBS buffer at room temperature. Cell monolayers were blocked with 0.1% PBS-Tween solution containing 10% bovine serum albumin for 1 hour. Subsequently, the monolayers were incubated with primary antibodies diluted in PBS-0.1% Tween/1% BSA at 4 degrees Celsius overnight. After 24 hours, the primary antibodies were removed and the fixed monolayers were washed three times with PBS-0.1% Tween/1% BSA. Cells were incubated with appropriate secondary antibodies diluted in PBS-0.1% Tween/1% BSA for one hour at room temperature and washed with three times with PBS. Cultures were then mounted with PermaFluor™ Aqueous Mounting Medium and counterstained with NucBlue Hoescht 33342. The cells were imaged with the Zeiss Axio Observer Z1 microscope with LD PlanNeoFluar objective lenses, and a Zeiss AxioCamMR3 camera was used for image acquisition. The images were processed through Zeiss Axiovision SE 64 Rel 4.8 and analyzed using Zeiss Axiovision version 4.9.1.0. The percentage of positive cells and standard deviation was estimated from at least five random fields of view.

Before Differentiation

Figure 2:
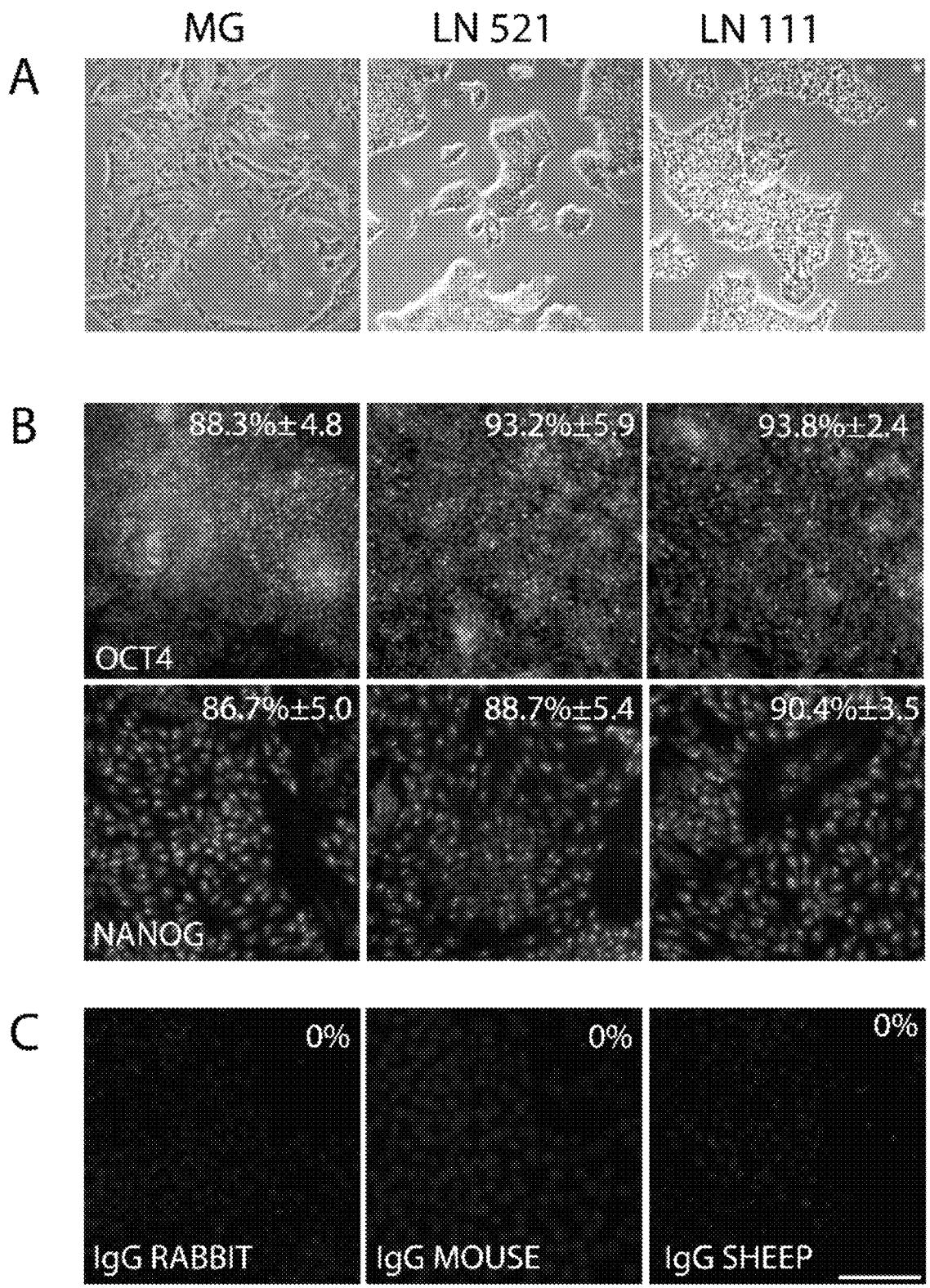
FIG. 2 is a set of 12 photomicrographs illustrating pluripotent stem cell morphology before and after differentiation on three different substrates: control media (MG); laminin-521 (LN 521); and a combination of laminin-521 and laminin-111 in a 1:3 ratio (LN 111). Control staining for IgG rabbit, mouse, and sheep antisera are also shown.

FIG. 2 is a set of 12 photomicrographs at 10× magnification, organized into three columns and four rows. The leftmost column is for the MG substrate, the middle column is for the LN-521 substrate, and the rightmost column is for the LN-511 substrate. Row A is a set of phase contrast images of pluripotent stem cell morphology on the three different substrates prior to the onset of differentiation. Row B is a set of photomicrographs showing the immunofluorescent staining of octamer 4 (OCT4) on the three different matrices prior to the onset of differentiation. Row C is a set of photomicrographs showing the immunofluorescent staining of Nanog protein on the three different matrices prior to the onset of differentiation. Row D is a set of photomicrographs showing immunoglobulin G control staining for rabbit, mouse and sheep antisera.

Cells on all three matrices adhered, proliferated, and differentiated into hepatocyte like cells (HLCs). After 24 hours post-replating, ESCs displayed appropriate character- istic cell morphology, including appropriate expression levels of stem cell associated markers OCT4 and Nanog, with subtle differences on each substrate, as seen in Rows A, B, and C of FIG. 1. Expression levels of OCT4 and Nanog among the substrates are also visible on the photomicrographs, and are listed in the table below.

| Substrate | Expression Levels | |
| --- | --- | --- |
| | OCT4 | Nanog |
| MG | 88.3% ± 4.8 | 86.7% ± 5.0 |
| LN-521 | 93.2% ± 5.9 | 88.7% ± 5.4 |
| LN-511 | 93.8% ± 2.4 | 90.4% ± 3.5 |

Differentiation Analysis

Twenty four hours post-replating, differentiation was initiated using a serum free procedure. Cell extracts were collected during differentiation and mRNA assessed on days 0, 3, 9, and 18. Of note, all differentiation procedures delivered cell populations that transited from pluripotency, through definitive endoderm, to hepatoblast like cells and subsequently hepatocytes as demonstrated by quantitative PCR. It should be remembered that the "LN-511" label refers to a substrate containing a blend of laminin-521 and laminin-111 at a 1:3 weight ratio.

Figure 3:
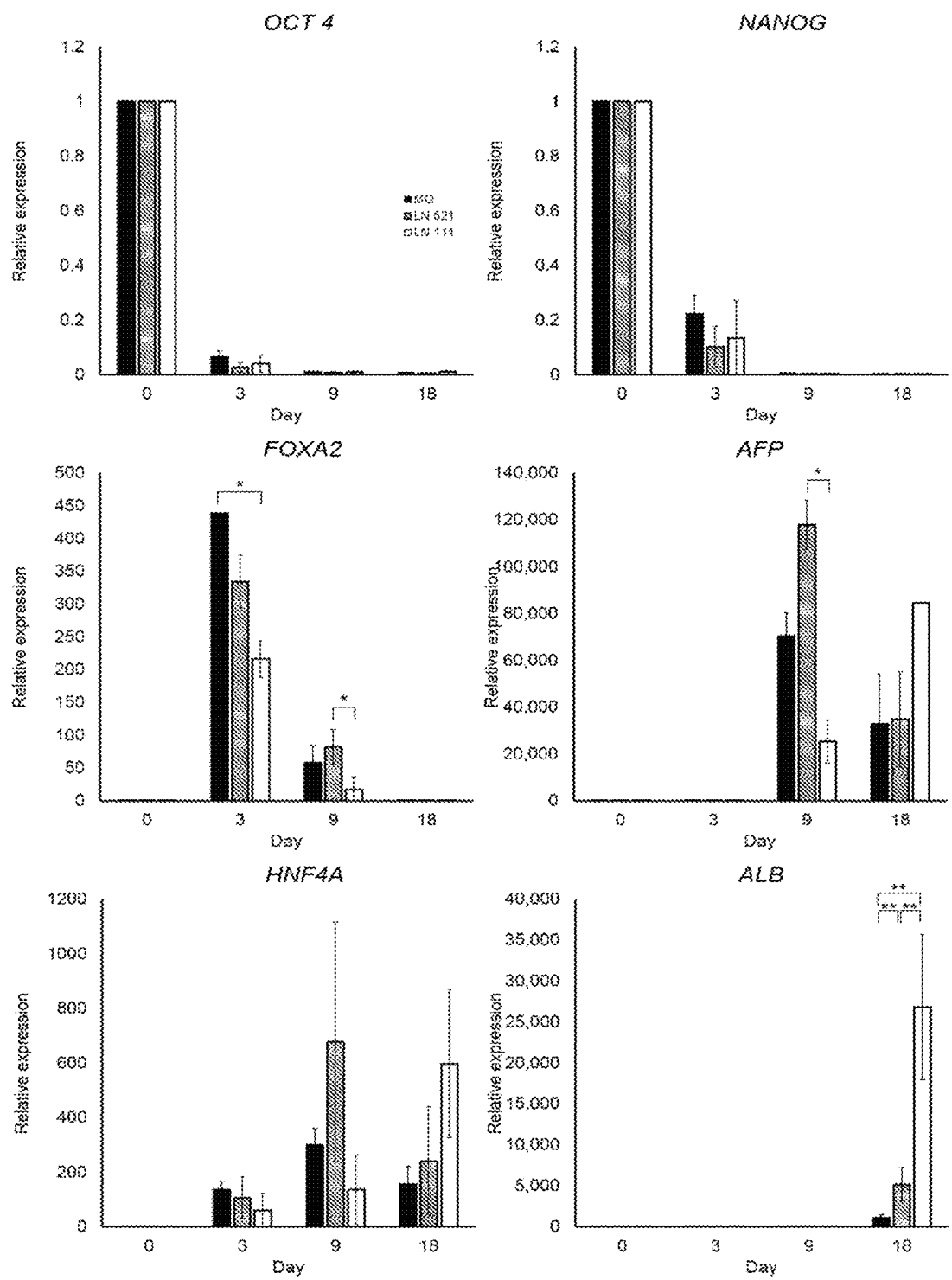
FIG. 3 is a set of six bar graphs of OCT4, Nanog, FOXA2, AFP, HNF4A, and ALB expression during differentiation on the three different substrates of FIG. 2. For each graph, the dark bar is MG; the dashed bar is LN 521, and the white bar is LN 111. The y-axis is relative expression, and the x-axis is days, with the four bars being days 0, 3, 9, and 18 of differentiation. Expression is normalized to the housekeeping gene GAPDH. Single asterisk (*) indicates p<0.05 and double asterisk (**) indicates p<0.01 as measured by one-way ANOVA with Tukey post-hoc test.

FIG. 3 is a set of six bar graphs showing gene expression during differentiation on the three substrates (MG, LN-521, and LN-511) for six different genes whose name is above each graph. Relative gene expression was normalized to the housekeeping gene GAPDH. As seen, pluripotency markers OCT4 and Nanog decreased over time on all substrates. Endoderm associated gene FOXA2 peaked on all substrates on day 3 and then decreased thereafter. Expression of alpha-fetoprotein (AFP) varied across all substrates. Cells on the MG substrate and the LN-521 substrate followed the same trend in expression, peaking on day 9 then decreasing at day 18. Conversely, cells on the LN-111 substrate gradually increased in AFP expression over time, peaking at day 18. HNF4A was detected at day 3 on all substrates, but by day 9, significant differences in expression patterns emerged. On the MG and LN-521 substrates, HNF4A was highest on day 9, decreasing by day 18, whereas HNF4A expression significantly increased on day 18 on the LN-511 substrate. Variation in HNF4A gene expression was observed between experimental replicates, however this did not appear to affect downstream differentiation and was not reflected in HNF4 protein levels. Expression of albumin (ALB) was upregulated from day 9 across all substrates. Levels of albumin from day 9 to day 18 saw the highest increase on the LN-511 substrate (approximately 10,000 fold), which was significant compared to the MG and LN-521 substrates (both p<0.001).

Hepatoblast Specification

Figure 4:
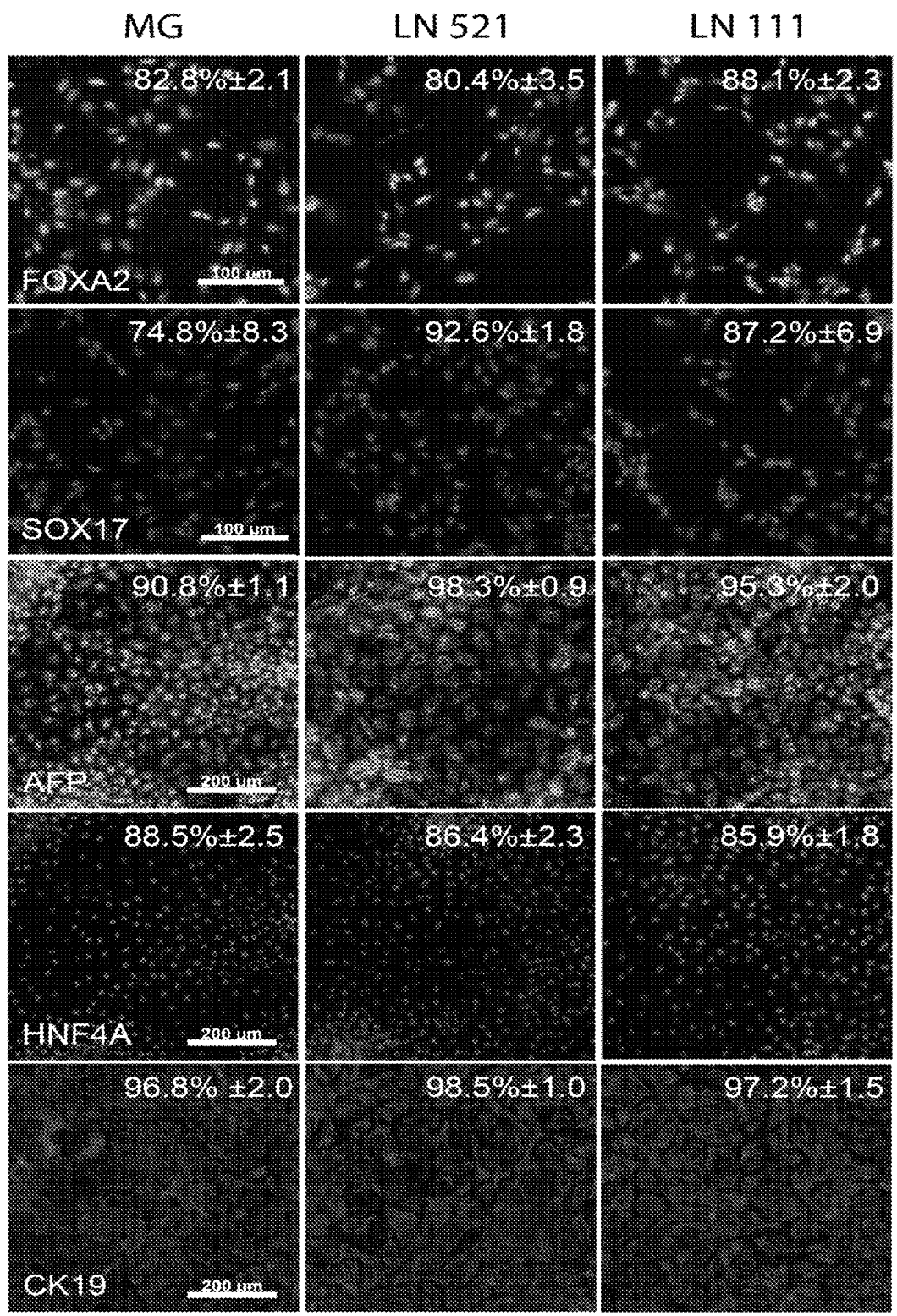
FIG. 4 is a set of 15 total photomicrographs of endoderm and hepatic cells grown on the three different substrates, 10×-20× magnification, showing the expression of FOXA2, SOX17, alpha-fetoprotein (AFP), hepatocyte nuclear factor 4 alpha (HNF4A), and cytokeratin 19 (CK19), on day 3 of differentiation. The percentage of positive cells and standard deviation is shown. Cells were counterstained with hoescht 33342.

Next, the efficiency of the differentiation process was measured. FIG. 4 is a set of 15 photomicrographs of endoderm and hepatic cells grown on the three different substrates, 10× or 20× magnification (indicated by scale), on day 3 of differentiation. The photomicrographs are organized into three columns, one for each substrate (MG, LN-521, and LN-111), and into five rows, one for each marker (FOXA2, SOX17, AFP, HNF4A, and cytokeratin 19 (CK19)). The percentage of positive cells and standard deviation for each marker are listed in the table below.

| Substrate | FOXA2 | SOX17 | AFP | HNF4A | CK19 |
|---|---|---|---|---|---|
| MG | 82.8% ± 2.1 | 74.8% ± 8.3 | 90.8% ± 1.1 | 88.5% ± 2.5 | 96.8% ± 2.0 |
| LN-521 | 80.4% ± 3.5 | 92.6% ± 1.8 | 98.3% ± 0.9 | 86.4% ± 2.3 | 98.5% ± 1.0 |
| LN-111 | 88.1% ± 2.3 | 87.2% ± 6.9 | 95.3% ± 2.0 | 85.9% ± 1.8 | 97.2% ± 1.5 |

FOXA2 was expressed on all substrates at day 3. The majority of cells on the MG, LN-521 and LN-111 substrates. SOX17 staining was more varied across the three substrates; it was lowest on MG and highest on LN-521. As cell differentiation progressed and hepatic fate was specified, cells began expressing high levels of hepatoblast markers. AFP, HNF4a, and CK19 were expressed in the majority of cells on all three substrates. Hepatoblast specification on all three substrates appeared equivalent and highly efficient, and the initial differences in hESC morphology observed on the three substrates did not appear to affect the kinetics or the efficiency of cellular differentiation using this procedure. However, an approximately 2-fold increase in cell size was observed in hepatocytes differentiated on the LN-521 and LN-511 substrates (see the CK19 photomicrographs). As shown, hepatoblast specification on all three matrices appeared equivalent and highly efficient. Any initial differences in hESC morphology observed on the three matrices did not appear to affect the kinetics, efficiency or cellular differentiation.

Hepatocyte Maturation

Post-hepatoblast specification, cell cultures were differentiated toward hepatocytes. Hepatocyte specification was assessed by immunostaining for albumin (ALB), E-cadherin (E CAD), cellular proliferation marker (Ki67), cytochrome p450 2D6 (CYP2D6), and cytochrome p450 3A4 (CYP3A4).

Figure 5:
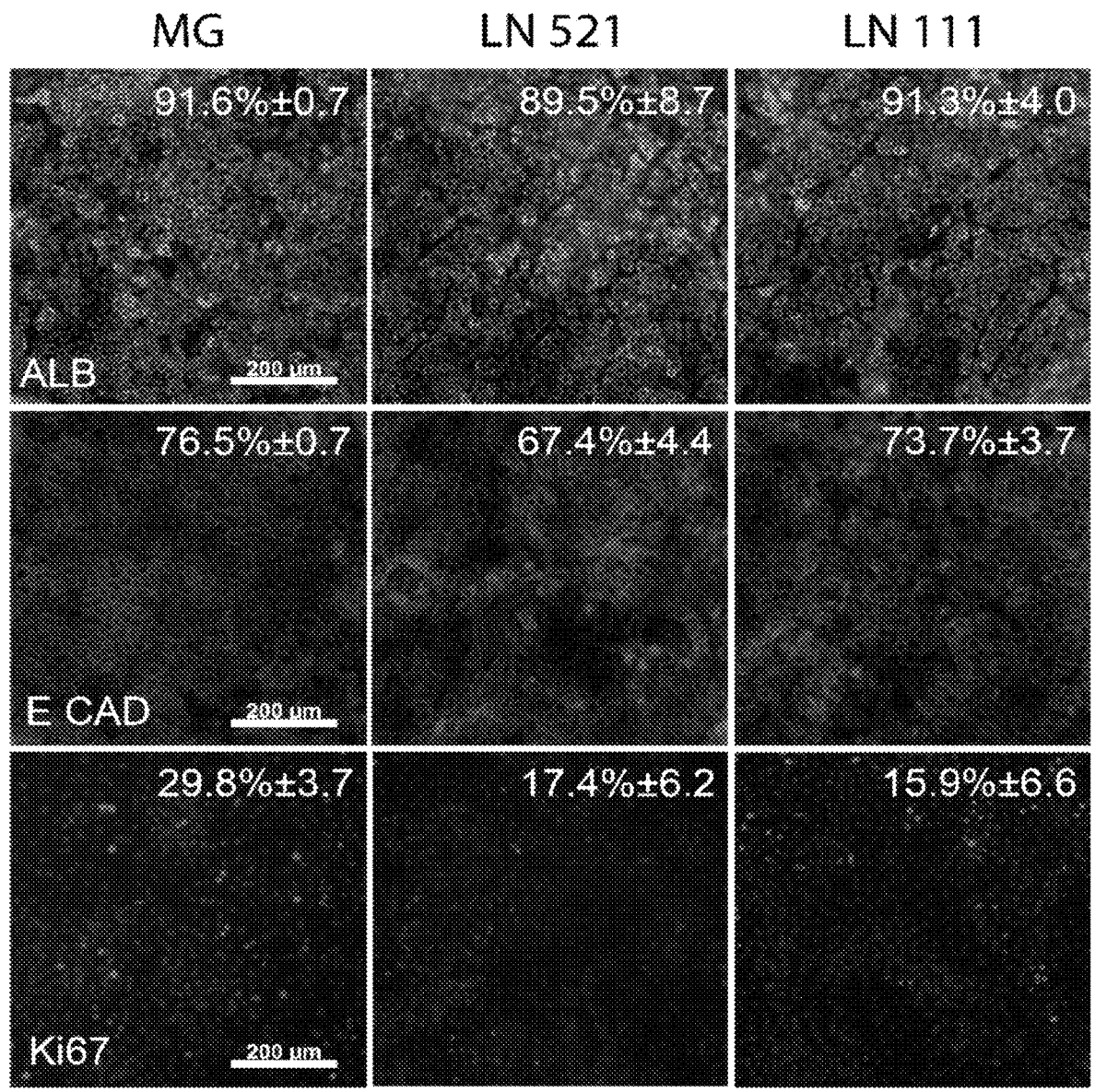
FIG. 5 is a set of nine photomicrographs of hepatocytes grown on the three different substrates of FIG. 2, 10× magnification, with expression of albumin (ALB), e-cadherin (E CAD), and cellular proliferation marker Ki67, on day 18 of differentiation. The percentage of positive cells and standard deviation is shown.

FIG. 5 is a set of nine photomicrographs of hepatic cells on day 18 of differentiation. The photomicrographs are organized into three columns, one for each substrate (MG, LN-521, and LN-111), and into three rows, one for each marker (ALB, E CAD, and Ki67). The percentage of positive cells and standard deviation for each marker are listed in the table below.

| Substrate | Albumin | E CAD | Ki67 |
|---|---|---|---|
| MG | 91.6% ± 0.7 | 76.5% ± 0.7 | 29.8% ± 3.7 |
| LN-521 | 89.5% ± 8.7 | 67.4% ± 4.4 | 17.4% ± 6.2 |
| LN-511 | 91.3% ± 4.0 | 73.7% ± 3.7 | 15.9% ± 6.6 |

Similar patterns of protein production between the matrigel and laminin populations were observed. Albumin staining was detected in cells on all three substrates, with the highest expression on the MG substrate and the lowest on the LN-521 substrate. E-cadherin (E CAD) is important in regulating hepatocyte cell to cell contact and involved in cell spatial regulation. Expression was highest on the MG and LN-111 substrates. However, on the LN-521 substrate foci with brighter staining were observed. While immunostaining studies showed equivalence between the populations, differences in cell division were observed on the different substrates with more cells undergoing proliferation on the MG substrate compared to the LN-521 and LN-111 substrates.

Hepatocyte Function

Given that cell organisation and cell division are important factors in hepatocyte function, hepatocyte metabolic capacity in vitro was studied. Stem cell derived hepatocytes were first examined for cytochrome P450 expression using well characterised antisera. CYP3A and CYP1A2 activity were measured from days 16-26 using pGlo technology. CYP activity was expressed as relative light units (RLU) per milliliter of media per milligram of protein. Levels of significance were measured by student t-test.

Figure 6:
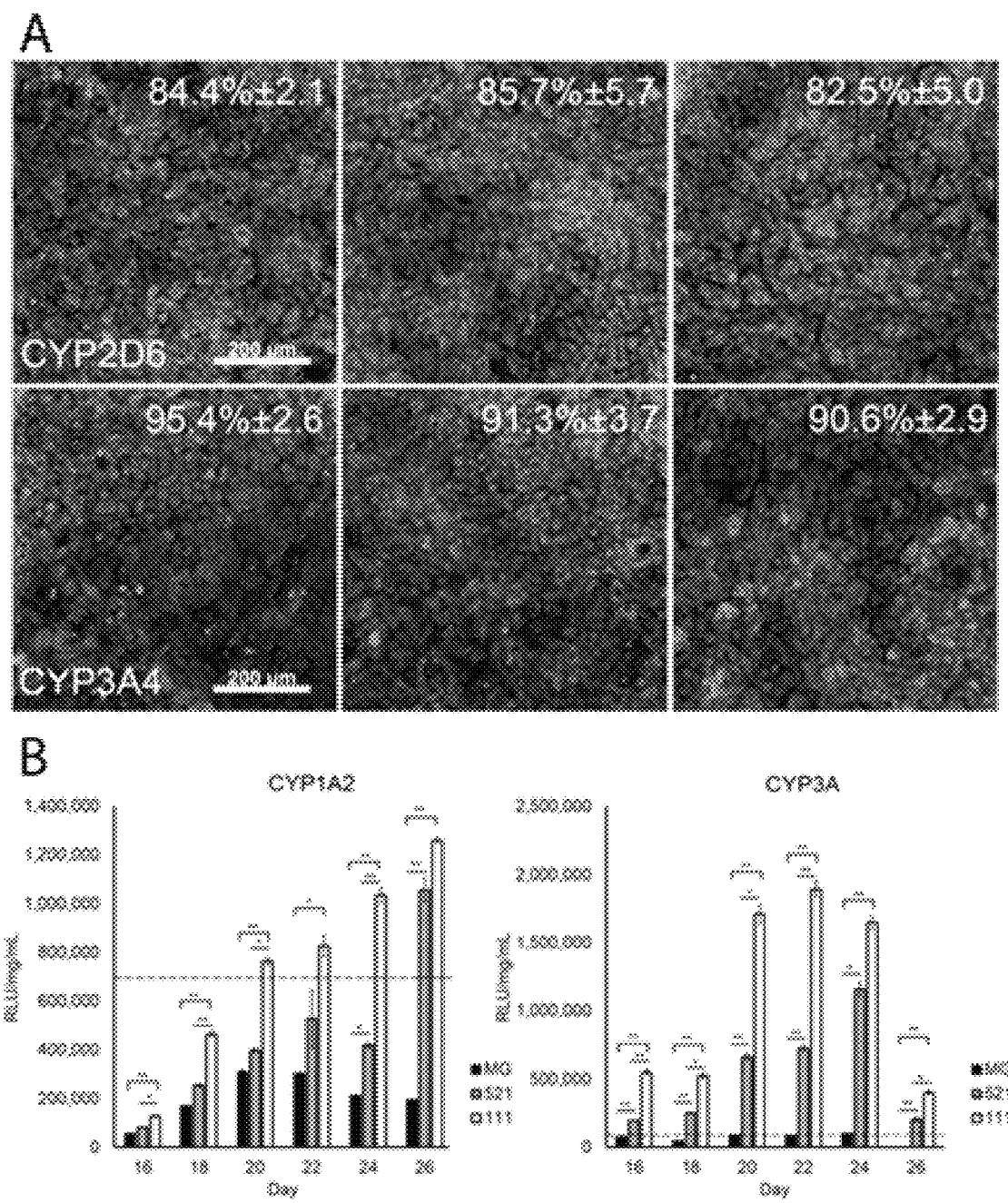
FIG. 6 is a set of six photomicrographs of hepatic cells grown on the three different substrates of FIG. 2, 10× magnification, with expression of CYP2D6 and CYP3A4, as well as corresponding bar graphs of metabolic activity of CYP1A2 and CYP3A. The percentage of positive cells and standard deviation is shown. On the two graphs, the y-axis is RLU/mg/mL, and the x-axis is days 16, 18, 20, 22, 24, and 26 of differentiation. Single asterisk (*) indicates p<0.05 and double asterisk (**) indicates p<0.01 as measured by one-way ANOVA with Bonferroni post-hoc test. The dotted line indicates the average CYP activity of primary hepatocytes in culture.

FIG. 6 is a set of six photomicrographs and two bar graphs of gene expression in hepatic cells. The photomicrographs are organized into three columns, one for each substrate (MG, LN-521, and LN-111), and into two rows, one for each marker (CYP2D6 and CYP3A4). The percentage of positive cells and standard deviation for each marker are listed in the table below.

| Substrate | CYP2D6 | CYP3A |
|---|---|---|
| MG | 84.4% ± 2.1 | 95.4% ± 2.6 |
| LN-521 | 85.7% ± 5.7 | 91.3% ± 3.7 |
| LN-111 | 82.5% ± 5.0 | 90.6% ± 2.9 |

All of the cells expressed high levels of each marker on each substrate. While protein expression appeared equivalent, stem cell hepatocyte CYP function varied dramatically, as seen in the two bar graphs. On the LN-111 substrate, CYP1A2 activity increased over time and was significantly higher than the MG substrate over all time points. On laminin-521, CYP1A2 activity was elevated and at all time was significantly greater than it was on the control. On day 26, cells on both laminin substrates demonstrated significant more CYP1A2 function than primary human hepatocytes in culture (indicated by dotted line). CYP3A function was increased by up to 25-fold on the LN-111 substrate. Cells on both laminin substrates exhibited significantly increased metabolic function relative to cells on the MG control substrate and primary hepatocytes.

Figure 7:
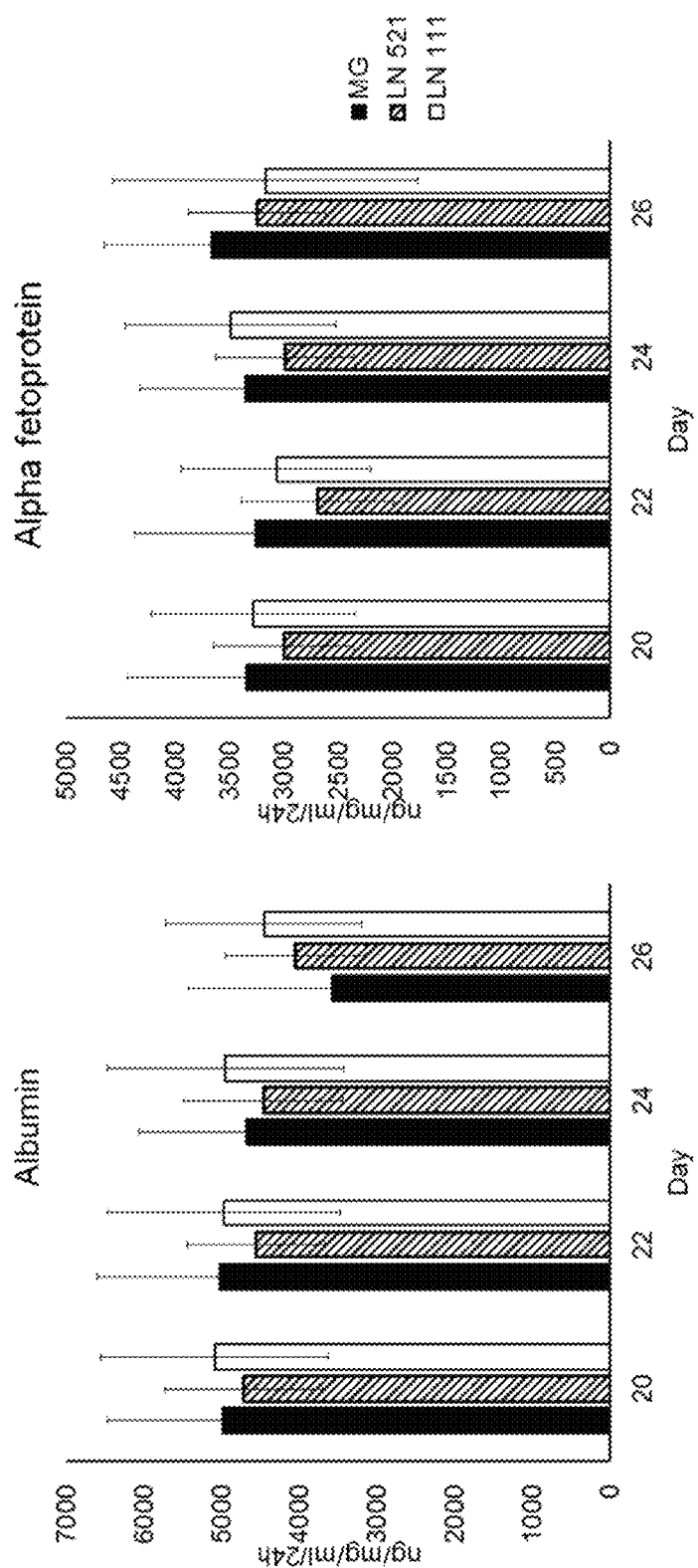
FIG. 7 is a set of two bar graphs showing production of albumin and alpha fetoprotein by hepatocytes cultured on the three different substrates of FIG. 6. For each graph, the dark bar is MG; the dashed bar is LN 521, and the white bar is LN 111. The y-axis is ng/mL/24 hours. The x-axis is days, with the four bars being days 20, 22, 24, and 26 of differentiation.

To determine whether these large changes in metabolic capacity correlated to increased protein production, the production of albumin and alpha fetoprotein (AFP) from hESC-derived and cryoplatable hepatocytes was quantified using commercially available enzyme-linked immunosorbent assay (ELISA) kits. The different media were collected at denoted time points during hESC differentiation, days 20-26. Primary hepatocyte media was harvested at 24 hours post plating onto commercially available medium or laminin coated surfaces. Samples were run in triplicate and measured on a FLUOStar Omega multi-mode microplate reader. Protein production was expressed as ng or µg of protein per milliliter of media, per milligram of protein. The results are shown in FIG. 7, where the expression of these two proteins was measured on days 20, 22, 24, and 26 of differentiation. Despite the large changes in metabolic capacity, no significant differences in albumin or AFP secretion was detected by ELISA. Thus, it is hypothesized that any differences were most likely due to differences in cell organization on the substrates.

Functional Organization

Figure 8:
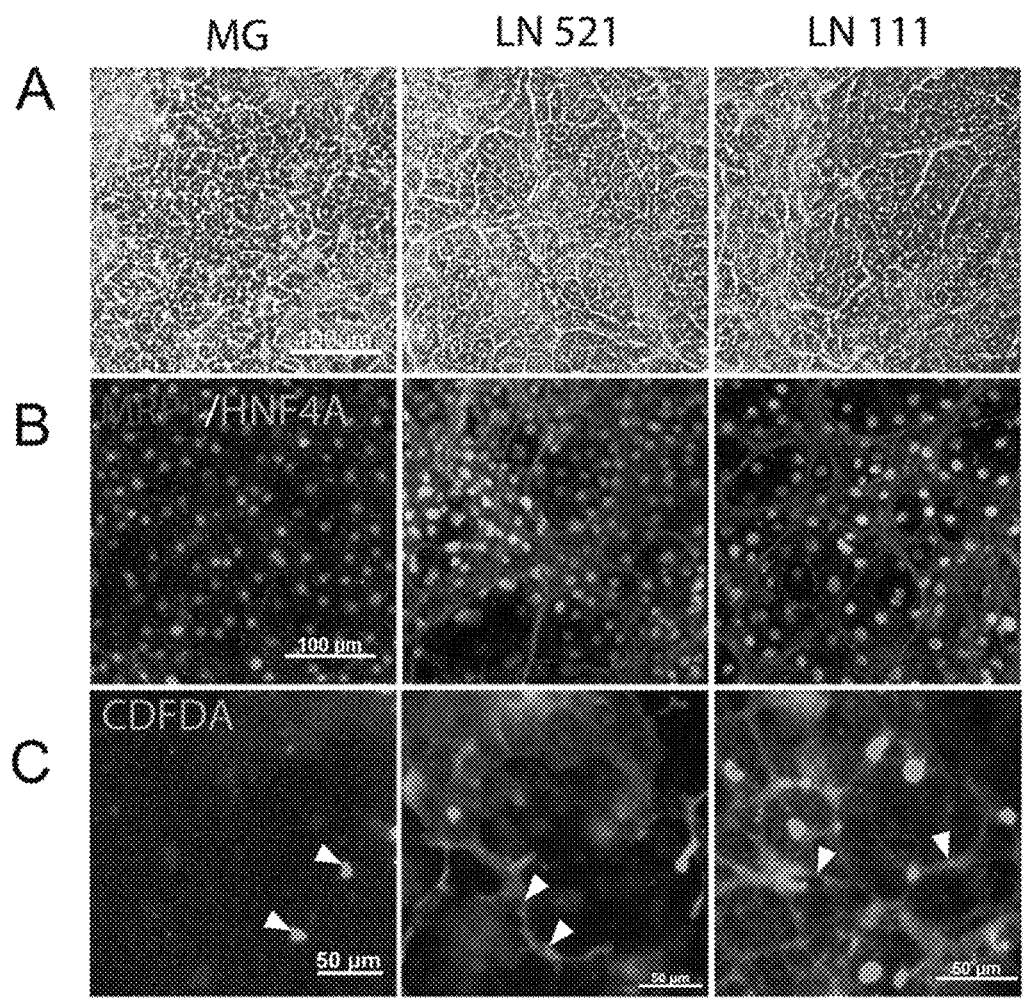
FIG. 8 is a set of nine photomicrographs of hepatic cells grown on the three different substrates of FIG. 2, 10× magnification, arranged in three rows. The uppermost row is a phase contrast image of the cells on day 24 of culture. The middle row is a co-staining of multidrug resistance associated protein (MRP-1) and HNF4a, using CDFDA staining. The green dots are HNF4a, and the red lines around the dots are MRP-1.

FIG. 8 is a set of nine photomicrographs from day 24 of differentiation. The photomicrographs are organized into three columns, one for each substrate (MG, LN-521, and LN-111), and into three rows.

The top row (A) of photomicrographs shows phase contrast images. Stem-cell derived hepatocytes cultured on the LN-521 and LN-111 substrates displayed a more primary hepatocyte-like appearance, often bi-nucleate with very pronounced nuclei. The phase contrast images also indicated hepatocytes were arranged in lobule-like structures within the culture dish, reminiscent of regenerating liver.

The middle row (B) shows co-immunostaining for MRP1 and HNF4a. Around these lobule structures, positive staining for MRP-1, an important basal membrane marker, was detected. Only hepatocytes differentiated on the LN-521 and LN-111 substrates exhibited networks of organised hepatocytes in vitro. This was in stark contrast to cells on the MG substrate, which displayed more individual and punctate staining.

To determine whether these cells were capable of biliary efflux, cells were treated with 5(6)-carboxy-2',7'-dichlorofluorescein diacetate (CDFDA), which was metabolised to fluorescent CDF and effluxed by multidrug resistance associated protein 2 (MRP2). hESC-derived hepatocytes were incubated with 2 µM of 5(6)-carboxy-2',7'dichlorofluorescein diacetate (CDFDA) for 30 minutes. Cultures were then washed with ice-cold PBS containing calcium and magnesium. Cells were either collected for imaging or retained for quantification of efflux. For fluorescent quantification, hepatic maturation was replaced and cells incubated at 37 degrees Celsius for 30 minutes. The efflux of CDFDA from cells into media was measured by fluorescence spectroscopy at 485/585 nm using a FLUOStar Omega multi-mode microplate reader.

The results are shown in the bottom row (C) of photomicrographs. Notably, cell organisation was paralleled by more active biliary efflux in cells differentiated on the LN-521 and LN-111 substrates versus the MG substrate.

Genome-Wide Analysis

The results discussed above demonstrated an improvement in the stem cell differentiation to hepatocytes on laminins. To understand which gene regulatory networks underpinned this, an extensive and unbiased bioinformatics analysis was performed. For this purpose, ESCs were differentiated on the MG, LN-521, and LN-511 substrates. It should be remembered that the "LN-511" label refers to a substrate containing a blend of laminin-521 and laminin-111 at a 1:3 weight ratio. The standard differentiation protocol was applied and whole-genome expression profiles of three independent experiments were analyzed. Data were compared to a previous study (Godoy et al., J. Hepatol., 2015 May 25, pii: S0168-8278(15)00340-2, doi: 10.1016/j.jhep.2015.05.013) which used freshly-isolated primary human hepatocytes (FH), ESCs and Matrigel®-differentiated hepatocyte-like cells (HLC, D17 and D21). These data were then compared to the stem-cell derived hepatocytes of the MG, LN-521, and LN-511 substrates (D24, L521 and L111 respectively).

Figure 9A:
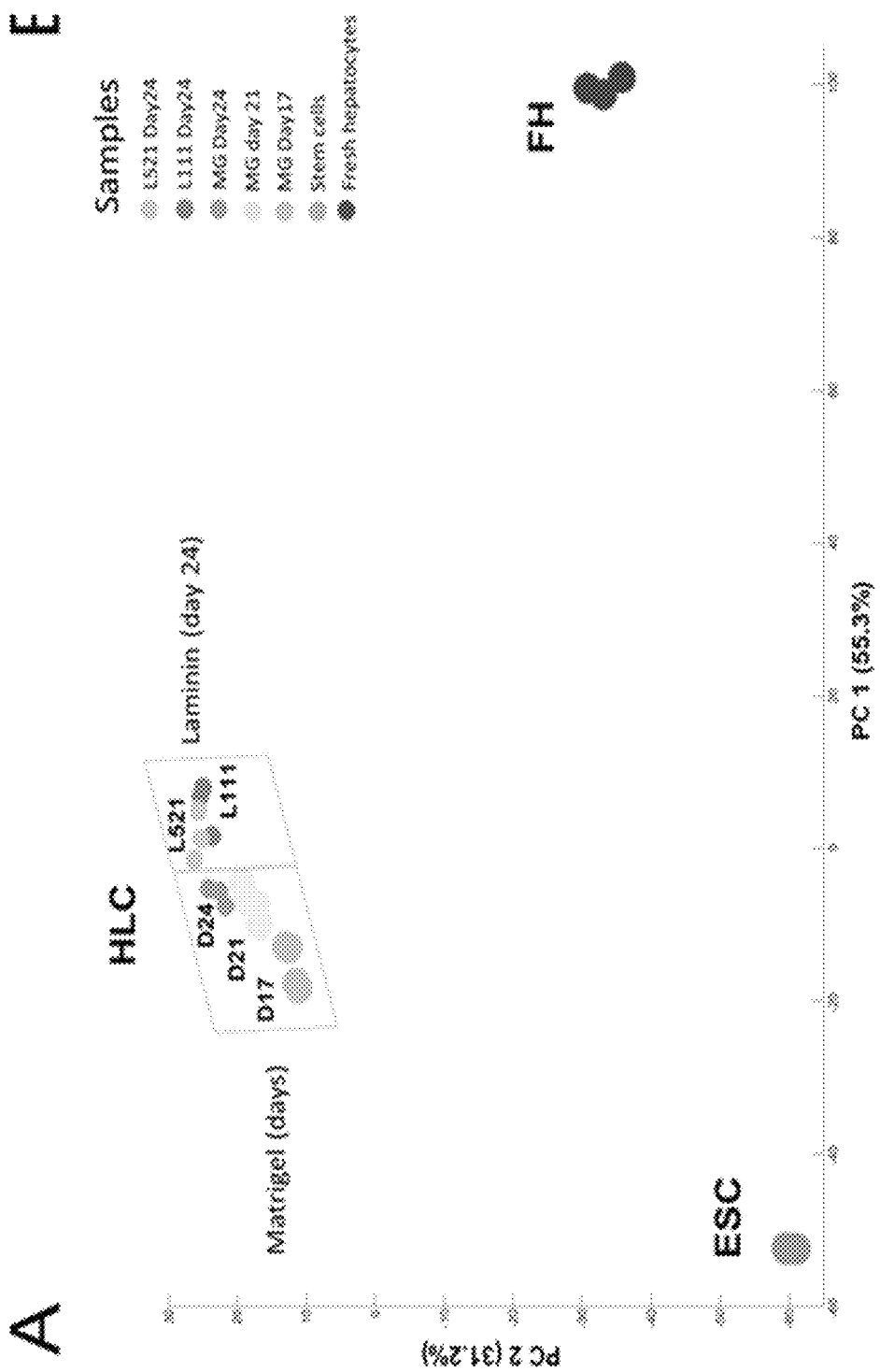
FIG. 9A is a principal component analysis of the 1,000 genes with highest variance in embryonic stem cells (ESC), freshly isolated primary human hepatocytes (FH), and hepatocyte-like cells (HLC) obtained from the three different substrates of FIG. 2. The two primary components (PC 1 and PC 2) together constituted 86.5% of variation. The y-axis is PC 2, and ranges from −60 to +30 in intervals of 10. The x-axis is PC 1, and ranges from −60 to +100 in intervals of 20.

FIG. 9A is a principal component analysis created via CellNet of the 1,000 genes with highest variance in ESC, FH and HLC differentiated in commercially available media for 17, 21 and 24 days and the LN-521 and LN-511 substrates for 24 days. The result indicated that laminin-directed differentiation shifted the resulting HLCs towards fresh hepatocytes (FH). The number of differentially expressed genes in the present study (556 between MG and LN-521 substrates, and 664 between MG and LN-111 substrates, FDR adjusted) could be considered as major.

Figure 9B:
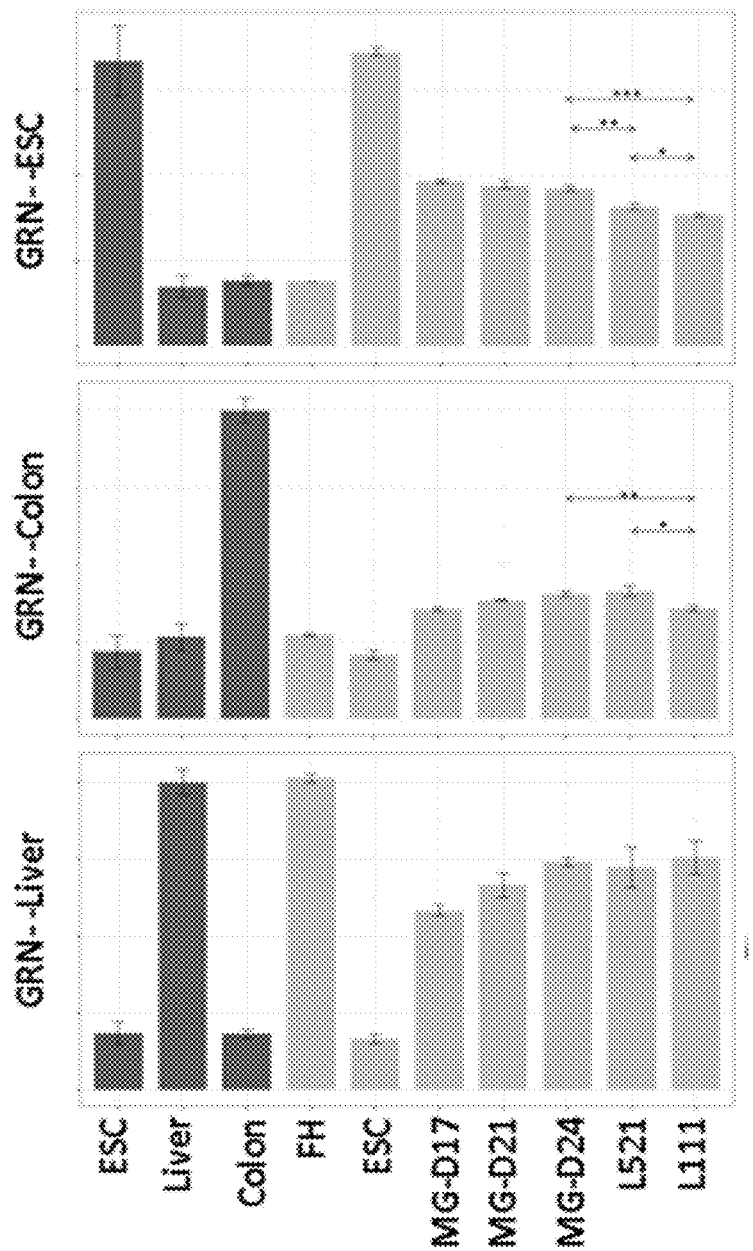
FIG. 9B is a set of three bar graphs showing the gene regulatory network statuses for the samples of FIG. 9A. The y-axis is the Gene Regulatory Network Score (GRN-Score), and is in units of % variance. The ESC, Liver, and Colon bars on the far left are the training scores, and represent the maximum possible score.

FIG. 9B illustrates the gene regulatory network status obtained from the gene expression profile in freshly-isolated primary human hepatocytes (FHs), ESC and control substrate differentiated hepatocyte-like cells (HLCs) in the three different substrates. The training scores for ESC, colon, and liver on the far left are shown in dark blue and represent the maximum scores for each cell/tissue. The scores for the queried samples (in light blue) are calculated in relation to the maximum cell/tissue specific scores. A significant decrease in the GRN-ESC score was seen in the LN-521 and LN-111 scores compared to the MG-differentiated scores. Of the two laminins, the LN-111 substrate showed a significantly stronger effect than the LN-521 substrate. The GRN-Colon score also significantly decreased between the laminin and MG HLCs. Again, the LN-111 substrate showed a significantly stronger effect than the LN-521 substrate. In contrast to the desired suppression of GRN-ESC and GRN-Colon scores, there was no significant improvement of the GRN-liver score by the laminin substrates compared to the control MG substrates. This result was in contrast to the data obtained for individual liver genes (HNF4a, albumin in FIG. 3) which showed a clear increase in the HLCs of the laminin substrates compared to the MG substrate. This discrepancy illustrates the importance of comparing genome-wide trends versus individual hand-picked genes in order to avoid misinterpretation.

Figure 9C:
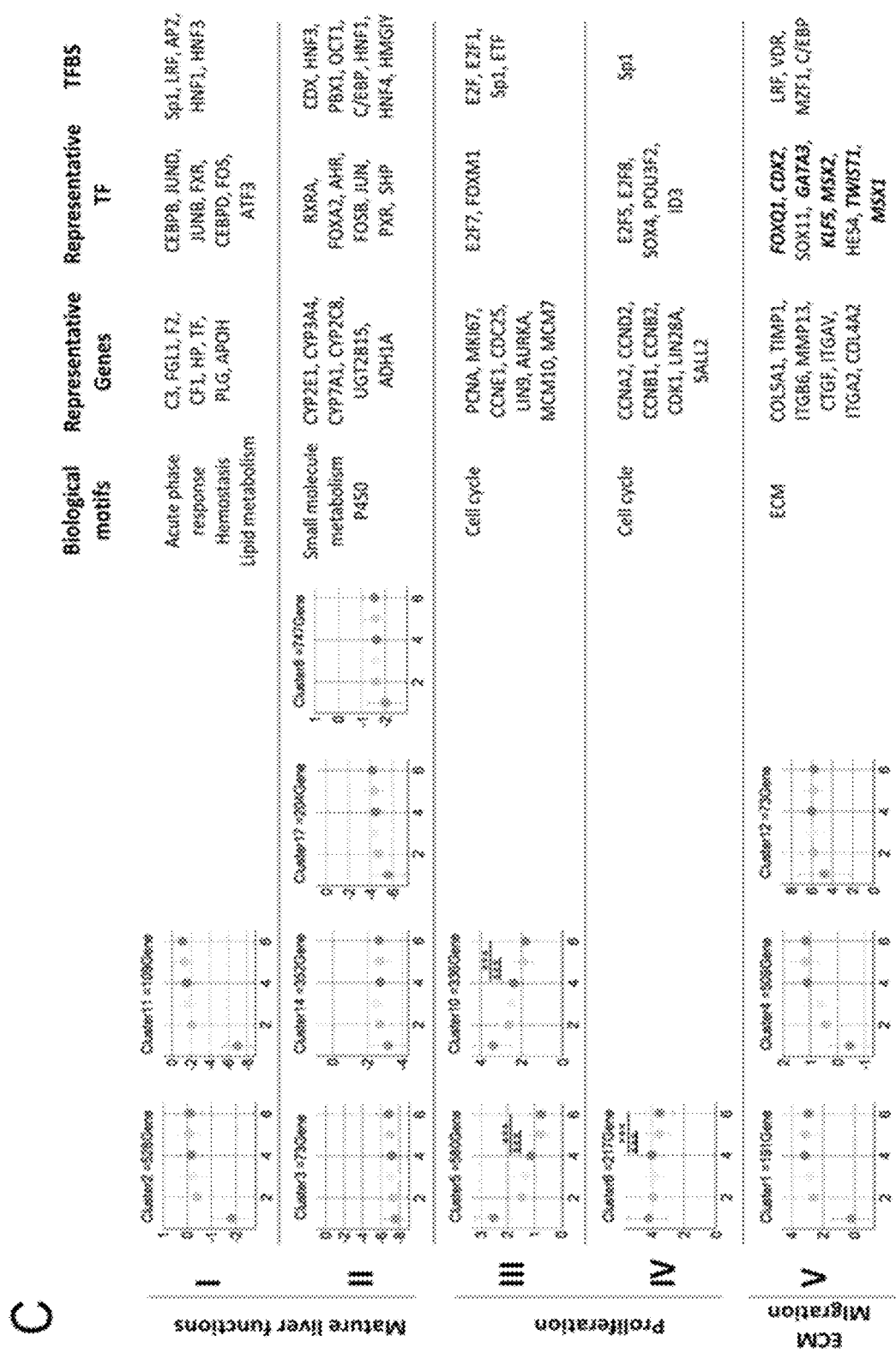
FIG. 9C is a set of clusters obtained using fuzzy clustering techniques and organized into three "superclusters". 12 bar graphs are shown. In each bar graph, the y-axis is the log 2 fold change, i.e. the multiple of the difference from the control.

FIG. 9C is a set of graphs generated after obtaining three superclusters using a fuzzy clustering technique disclosed in the Godoy 2015 reference. Genes with similar expression patterns in hepatocyte like cells were grouped into three superclusters associated with three different functions: mature liver functions (rows I and II); proliferation (row III) and extracellular matrix (ECM)/migration (rows IV and V). With respect to each individual gene cluster graph (e.g., cluster 2=528 gene), six different samples are plotted to show expression levels of each gene. In each gene cluster graph, the first dot (from the left) is representative of human embryonic stem cells (hESCs), the second dot is stem cell-derived hepatocyte-like cells (HLCs) grown on the MG substrate after 17 days; the third dot is stem cell-derived HLCs grown on the MG substrate after 21 days; the fourth dot is stem cell-derived HLCs grown on the MG substrate after 24 days; the fifth dot is stem cell-derived HLCs grown on the LN-521 substrate after 24 days; and the sixth dot is stem cell-derived HLCs grown on the LN-111 mixed substrate after 24 days. For example, for row I, gene cluster 2=528 gene, hESCs have an extremely low expression level (about −1.75) as compared to the expression level of stem cell-derived hepatocyte-like cells grown on the LN-521 substrate after 24 days (about 0). Tables of these approximate expression level results are listed below, with the row number listed in parentheses after the cluster name. Also listed in FIG. 9C are the associated biological motifs with the genes, a selection of representative genes, a selection of representative transcription factors, and a selection of transcription factor binding sites. As seen in the individual graphs, in all three proliferation-associated clusters, laminin lead to a significantly stronger gene expression suppression in HLCs than the control media.

| Sample Type | Mean Expression Level |
|---|---|
| Cluster 2 = 528 gene (I) | |
| hESC | −1.75 |
| MG (day 17) | −0.5 |
| MG (day 21) | −0.25 |

| Sample Type | Mean Expression Level |
|---|---|
| MG (day 24) | −0.25 |
| LN-521 (day 24) | 0 |
| LN-111 (day 24) | 0 |
| Cluster 11 = 108 gene (I) | |
| hESC | −7 |
| MG (day 17) | −2 |
| MG (day 21) | −2 |
| MG (day 24) | −1.75 |
| LN-521 (day 24) | −1 |
| LN-111 (day 24) | −1 |
| Cluster 3 = 73 gene (II) | |
| hESC | −7.5 |
| MG (day 17) | −7 |
| MG (day 21) | −7 |
| MG (day 24) | −7 |
| LN-521 (day 24) | −7 |
| LN-111 (day 24) | −6.5 |
| Cluster 14 = 352 gene (II) | |
| hESC | −3 |
| MG (day 17) | −2.5 |
| MG (day 21) | −2.5 |
| MG (day 24) | −2.5 |
| LN-521 (day 24) | −2.5 |
| LN-111 (day 24) | −2.5 |
| Cluster 17 = 204 gene (II) | |
| hESC | −5.5 |
| MG (day 17) | −4.5 |
| MG (day 21) | −4 |
| MG (day 24) | −4 |
| LN-521 (day 24) | −4 |
| LN-111 (day 24) | −4 |
| Cluster 8 = 747 gene (II) | |
| hESC | −2 |
| MG (day 17) | −0.75 |
| MG (day 21) | −0.5 |
| MG (day 24) | −0.75 |
| LN-521 (day 24) | −0.5 |
| LN-111 (day 24) | −0.5 |
| Cluster 5 = 580 gene (III) | |
| hESC | 2.5 |
| MG (day 17) | 1.5 |
| MG (day 21) | 1.25 |
| MG (day 24) | 1.1 |
| LN-521 (day 24) | 0.9 |
| LN-111 (day 24) | 0.9 |
| Cluster 10 = 336 gene (III) | |
| hESC | 3.5 |
| MG (day 17) | 2.5 |
| MG (day 21) | 2.25 |
| MG (day 24) | 2.25 |
| LN-521 (day 24) | 2 |
| LN-111 (day 24) | 2 |
| Cluster 6 = 217 gene (IV) | |
| hESC | 4.1 |
| MG (day 17) | 4 |
| MG (day 21) | 4 |
| MG (day 24) | 4 |
| LN-521 (day 24) | 3.75 |
| LN-111 (day 24) | 3.75 |
| Cluster 1 = 191 gene (V) | |
| hESC | 0.25 |
| MG (day 17) | 2.25 |
| MG (day 21) | 2.5 |
| MG (day 24) | 3 |
| LN-521 (day 24) | 3 |
| LN-111 (day 24) | 2.5 |
| Cluster 4 = 509 gene (V) | |
| hESC | −0.5 |
| MG (day 17) | 0.5 |
| MG (day 21) | 0.75 |
| MG (day 24) | 1 |
| LN-521 (day 24) | 1.25 |
| LN-111 (day 24) | 1.25 |
| Cluster 12 = 73 gene (V) | |
| hESC | 4.5 |
| MG (day 17) | 6 |
| MG (day 21) | 6 |
| MG (day 24) | 6 |
| LN-521 (day 24) | 6 |
| LN-111 (day 24) | 6 |

Clustering of genes with similar expression patterns in HLCs generated three superclusters representing the motifs "mature liver functions," "proliferation," and "extracellular matrix (ECM)/migration." The KEGG and GO motifs are overrepresented in each gene cluster. Representative genes for each cluster and motif are also indicated. Genes listed in italics of Cluster V were expressed in lower levels in HLCs on the LN-111 substrate compared to the control MG substrate. Significant differences in mean gene expression levels were observed between the control MG substrate and the LN-521 and LN-111 substrates in clusters 5, 10 and 6, which correspond to the supercluster "proliferation." In all three proliferation-associated clusters, the laminin substrates led to a significantly stronger suppression than the MG substrate (clusters III and IV; FIG. 7 c). Within the "mature liver functions" clusters, several individual genes can be identified for which the laminin substrates allowed a higher expression compared to the control Matrigel® MG substrate, e.g. complement component 3 (C3), complement factor I (CF-I), plasminogen (PLG) and FXR (NR1H4) (Suppl. Table X), but as a gene cluster no significant difference was obtained.

Figure 10:
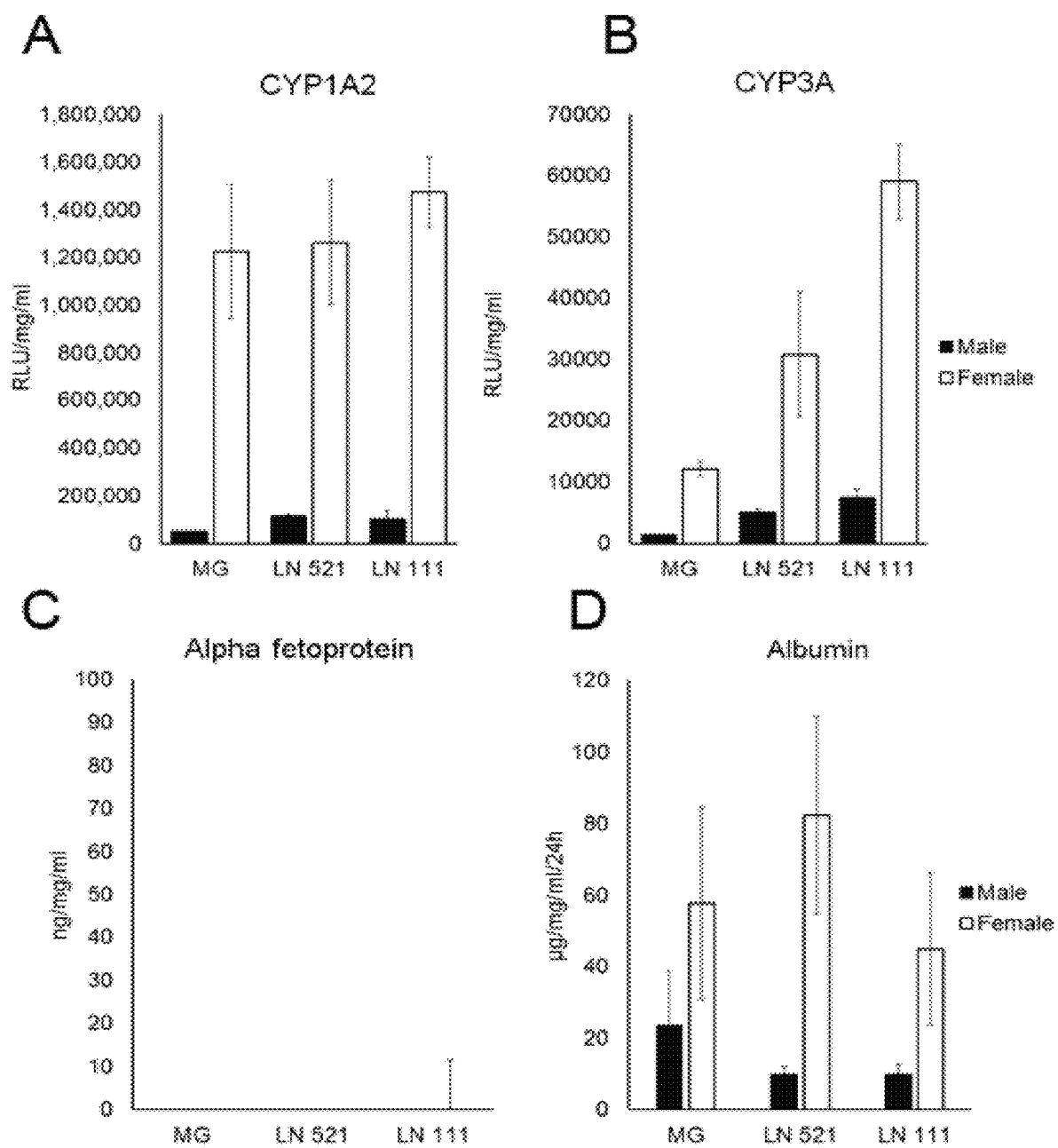
FIG. 10 is a set of bar graphs illustrating CYP1A2, CYP3A, alpha fetoprotein, and albumin expression in primary human hepatocytes plated on the three substrates of FIG. 2 and examined for metabolic competence after 48 hours. The y-axis for the CYP1A2 and CYP3A graphs is RLU/mg/mL. The y-axis for the alpha fetoprotein graph is ng/mg/mL. The y-axis for the albumin graph is µg/mg/ml/24 hours. In all four bar graphs, the black bar is male hepatocytes, and the white bar is female hepatocytes.

FIG. 10 is a set of four bar graphs illustrating primary human hepatocyte metabolism and protein production. Primary human hepatocytes (PHHs) from males and females were plated onto the MG, LN-521, and LN-111 substrates and examined for metabolic competence 48 hours later. CYP1A2 and CYP3A activity was increased on the laminin-containing substrates relative to the control MG substrate in both male (black bars) and female (white bars) PHHs. PHH albumin and alpha fetoprotein secretion were analysed by ELISA. Alpha fetoprotein was not produced at detectable levels and albumin production was enhanced on the LN-521 substrate in female PHHs.

Discussion

Three different substrates were tested, one the control Matrigel® substrate, and the other two containing laminins. While similar numbers of stem cell derived hepatocytes were produced on the three substrates, overt differences were observed in their cell assembly, organisation and function. By mimicking key elements of the liver cell niche, using two laminin isoforms, hepatocyte differentiation was dramatically improved, significantly enhancing cell organisation and function. Notably, CYP1A2 and CYP3A function were equivalent or superior to primary human hepatocytes when stem cell derived hepatocytes were cultured on the laminins, and they remained stable for several days in culture. Enhanced hepatocyte organisation on both laminins was evidenced by MRP1 staining, and resulted in improved canalicular excretion of CDFDA, suggesting a mature feature of stem cell derived hepatocytes in vitro These observations were consistent with better hepatocyte organisation and CYP P450 activities in cell populations differentiated on the laminin-containing substrates. Given the different roles that laminin plays in liver biology, studies were extended to current gold standard sources, primary hepatocytes from male and female donors. Notably, as was observed for hESC hepatocytes, laminin coated surfaces better supported CYP p450 activity, but did not significantly improve albumin secretion.

Since analysis of some selected liver markers suggested an improvement of liver differentiation when using laminin substrates compared to Matrigel®, genome-wide expression analysis was performed. A first goal was to answer whether different substrates/matrices caused dramatic or only minor changes in overall gene expression. Previous studies have shown that the type of matrix can cause major phenotypic alteration such as differences in cell polarity and sensitivity to apoptosis. Considering the number of differentially expressed genes in the present study (556 between the Matrigel® and the LN-521 substrates, and 664 between the Matrigel and the LN-111 blended substrates, FDR adjusted) the difference may be considered as major. It can be concluded that the laminin-containing substrates imparted three specific features compared to the Matrigel® control substrate. First, expression of stemness genes was more effectively suppressed, with a four-fold reduction in stem cell markers LIN28A and c-kit on laminins. Second, the blend of laminin-521 and laminin-111 more efficiently suppressed proliferation-associated gene expression. Third, induction of unwanted colon-associated and fibroblast-associate gene expression, which is an inherent side effect of the currently used hepatocyte differentiation protocols, was ameliorated by laminin-111. Therefore, genome-wide analysis clearly identified improvement of HLCs differentiated on laminin-containing substrates. Importantly, individual genes where the presence of laminin-111 improved the hepatocyte differentiation can be identified. For example, C3, haptoglobin, plasminogen and the transcription factor FXR increased at least 2-fold on the laminin-111-containing substrate compared to the Matrigel® substrate.

The present results showed the supportive properties of recombinant laminins in the context of stem-cell derived hepatocyte differentiation and metabolic function. hESC-derived hepatocytes displayed improved morphology, organisation, stability and cell function on human laminins, which was comparable to male and female primary hepatocytes.

Example 2

Stem-cell derived hepatocytes were produced from human embryonic stem cells on three different substrates. The first substrate was pure laminin-521 (LN-521). The second substrate was a mix of laminin-521 and laminin-221 in a weight ratio of 1:3 (221 (1:3)), i.e. three times more laminin-221. The third substrate was a mix of laminin-221 and laminin-521 in a weight ratio of 1:1 (221 (1:1)). At day 18, cells were fixed and stained for multidrug resistance protein 1 (MPR1).

Figure 11:
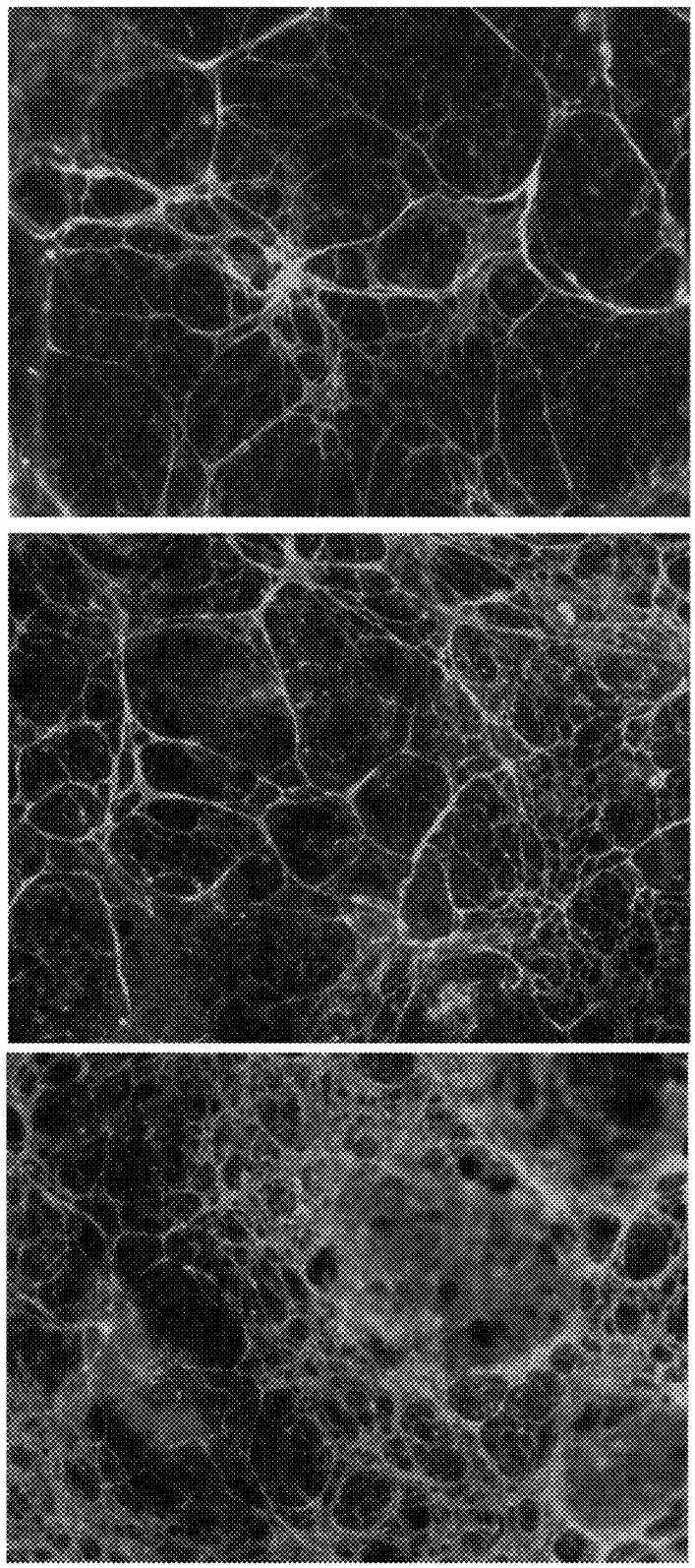
FIG. 11 is a set of three photomicrographs of stem cell derived hepatocytes grown on laminin-221/laminin-521 at a ratio of 1:3, laminin-221/laminin-521 at a ratio of 1:1, and laminin-521, stained for multidrug resistance protein 1 (MPR-1) after 18 days.
Figure 12:
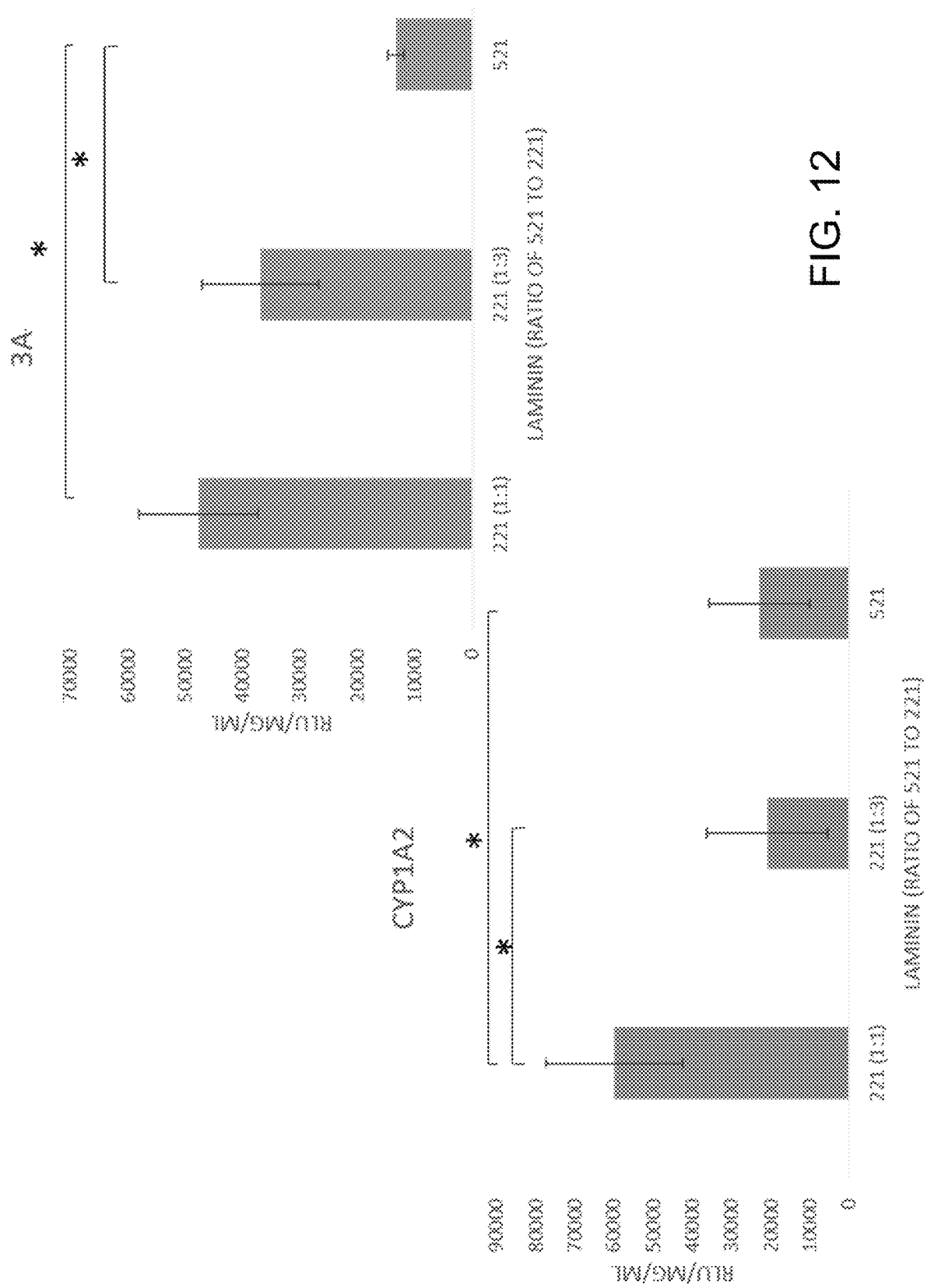
FIG. 12 is a set of two bar graphs illustrating CYP1A2 and CYP3A activity of stem cell derived hepatocytes on laminin-221/laminin-521 at a ratio of 1:3, laminin-221/laminin-521 at a ratio of 1:1, and laminin-521, stained with MPR-1 after 18 days.

FIG. 11 shows photomicrographs of the three substrates. Cells plated on the 221 (1:3) substrate demonstrated more complex tissue organisation than those plated on the LN-521 or 221 (1:1) substrates. This was also paralleled by cell function, as seen in FIG. 12. Stem-cell derived hepatocytes replated on the 221 (1:3) substrate were superior in terms of function when compared to the other two substrates.

Example 3

Stem-cell derived hepatocytes were produced from human embryonic stem cells on three different substrates. The first substrate was pure laminin-521 (LN-521). The second substrate was a mix of laminin-521 and laminin-221 in a weight ratio of 1:3 (221 (1:3)). The third substrate was a mix of laminin-221 and laminin-521 in a weight ratio of 1:1 (221 (1:1)). The Cameron procedure and the Avior procedure were compared to each other.

Figure 13:
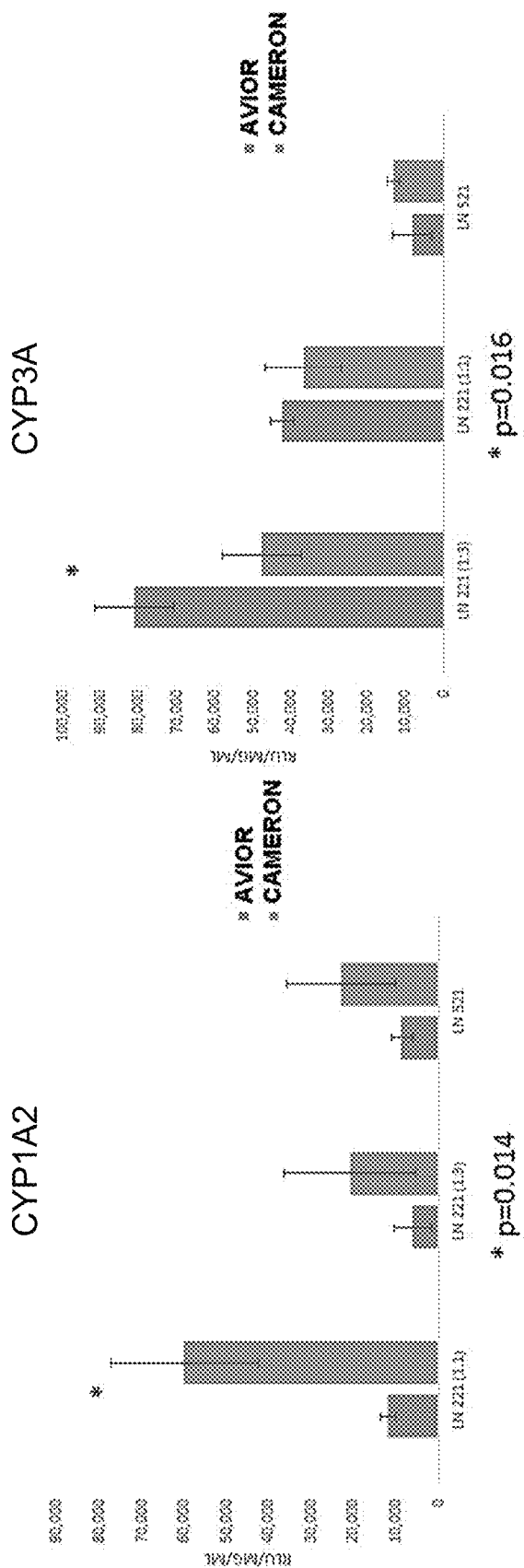
FIG. 13 is a set of graphs illustrating how Avior and Cameron differentiation procedures affected stem cell derived hepatocytes in culture on substrates of laminin-221/laminin-521 in a 1:3 ratio, laminin-221/laminin-521 in a 1:1 ratio, and pure laminin-521. For both graphs, the y-axis is RLU/mg/mL. For each substrate, the Avior procedure result is on the left, and the Cameron procedure result is on the right.

FIG. 13 is a set of two bar graphs showing hepatocyte function of the two procedures. In particular, the Avior procedure claims that the use of two inductive components, vitamin K (MK4) and lithocholic acid (LCA), dramatically improved hepatocyte differentiation. Such benefits were not observed using both MK4 and LCA.

Cells plated on the 221 (1:3) substrate performed better than those plated on the LN-521 or 221 (1:1) substrates. Notably, when adult hepatocyte function (CYP1A2) was measured, stem cell derived hepatocytes via the Cameron procedure performed better than those delivered by the Avior procedure. When fetal and adult liver function (CYP3A) was measured, the Avior procedure demonstrated better performance. LCA and MK4 elicited major toxic effects on stem cell derived hepatocytes resulting in cell death at day 18 using the Avior procedure. Typically stem cell derived hepatocytes display function and viability for 27 days in the differentiation process, indicating the Cameron procedure yields more stable hepatocyte and adult like populations in vitro when compared to the Avior procedure.

Example 4

MAN12 cells, a GMP grade cell line, were plated on three different substrates. The first substrate was Matrigel® (MG), and served as a control. The second substrate was coated with 5 micrograms per square centimeter ($\mu g/cm^2$) of laminin-521 (LN-521). The third substrate was coated with 5 $\mu g/cm^2$ of a blend of laminin-521 and laminin-111 at a 1:3 weight ratio (Biolamina, Sweden) (abbreviated here as LN-111). The cells were then differentiated according to the Cameron protocol.

Figure 14:
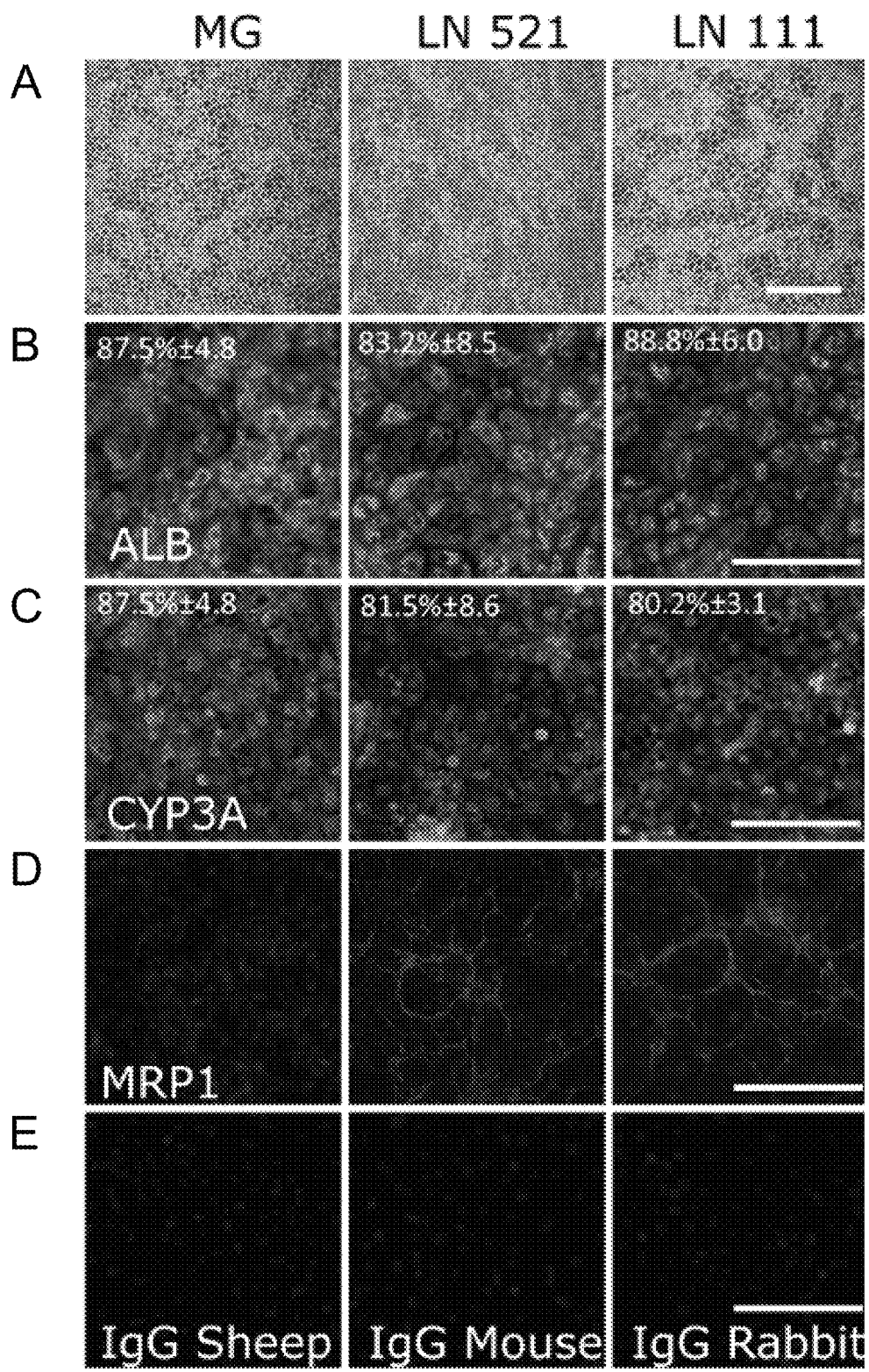
FIG. 14 is a set of 15 total photomicrographs of MAN12 cells grown on the three different substrates, stained for various markers.

FIG. 14 is a set of 15 photomicrographs at 10× magnification, organized into three columns and five rows, taken on Day 24 of differentiation. The leftmost column is for the MG substrate, the middle column is for the LN-521 substrate, and the rightmost column is for the LN-111 substrate. Row A is a set of phase contrast images of morphology. The scale bars are 200 µm. Row B is a set of photomicrographs showing the immunofluorescent staining of albumin (ALB) on the three different matrices. Row C is a set of photomicrographs showing the immunofluorescent staining of cytochrome P450 3A (CYP3A). Row D is a set of photomicrographs showing the immunofluorescent staining of multidrug resistance protein 1 (MRP1). Row E is a set of photomicrographs showing immunoglobulin G control staining for sheep, mouse, and rabbit antisera.

Figure 15:
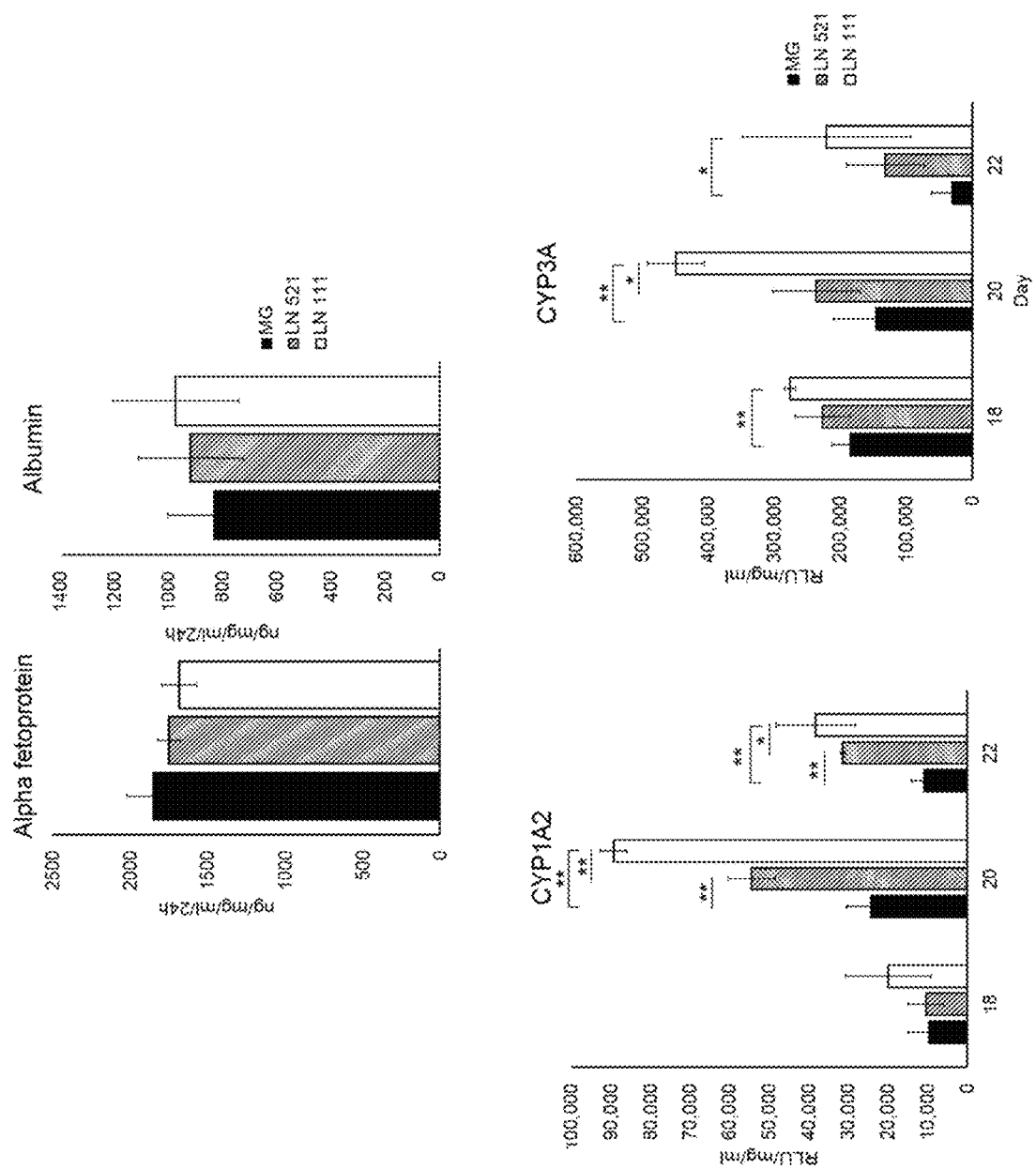
FIG. 15 is a set of four bar graphs of alpha fetoprotein, albumin, CYP1A2, and CYP3A expression during differentiation on the three different substrates of FIG. 14. For each graph, the dark bar is MG; the dashed bar is LN 521, and the white bar is LN 111. The y-axis for the alpha fetoprotein and albumin graphs is ng/mg/mL/24 hours. The y-axis for the CYP1A2 and CYP3A graphs is RLU/mg/ml. Single asterisk (*) indicates p<0.05 and double asterisk (**) indicates p<0.01 as measured by one-way ANOVA with Tukey post-hoc test.

FIG. 15 is a set of four bar graphs. The first row of two graphs show hepatocyte protein secretion for alpha fetoprotein and albumin as analyzed by ELISA on day 24 of differentiation (n=3). No significant differences were observed across the three matrices. The second row of two graphs show the metabolic function of CYP p450 activity on days 18, 20, and 24 for CYP1A2 and CYP3A activity. The percentage of positive cells and standard deviation for two markers are listed in the table below.

| Substrate | ALB | CYP3A |
| --- | --- | --- |
| MG | 87.5% ± 4.8 | 87.5% ± 4.8 |
| LN-521 | 83.3% ± 8.5 | 81.5% ± 8.6 |
| LN-511 | 88.8% ± 6.0 | 80.2% ± 3.1 |

Example 5

MAN11 cells, another GMP grade cell line, were plated on three different substrates. The first substrate was Matrigel® (MG), and served as a control. The second substrate was coated with 5 micrograms per square centimeter (µg/cm$^2$) of laminin-521 (LN-521). The third substrate was coated with 5 µg/cm$^2$ of a blend of laminin-521 and laminin-111 at a 1:3 weight ratio (Biolamina, Sweden) (abbreviated here as LN-111). The cells were then differentiated according to the Cameron protocol.

Figure 16:
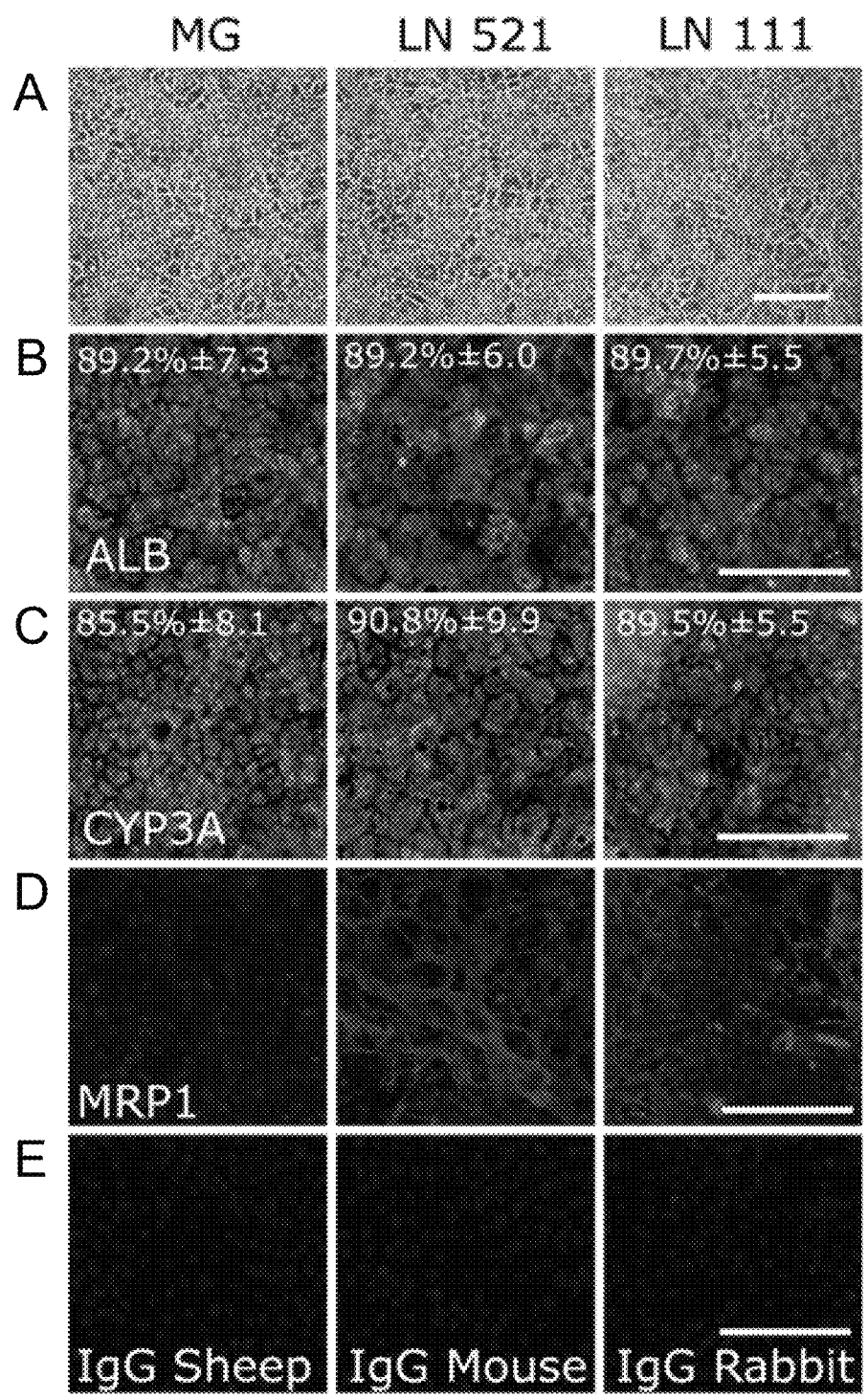
FIG. 16 is a set of 15 total photomicrographs of MAN11 cells grown on the three different substrates, stained for various markers.

FIG. 16 is a set of 15 photomicrographs at 10× magnification, organized into three columns and five rows. The leftmost column is for the MG substrate, the middle column is for the LN-521 substrate, and the rightmost column is for the LN-111 substrate. Row A is a set of phase contrast images of morphology. The scale bars are 200 µm. Row B is a set of photomicrographs showing the immunofluorescent staining of albumin (ALB) on the three different matrices. Row C is a set of photomicrographs showing the immunofluorescent staining of cytochrome P450 3A (CYP3A). Row D is a set of photomicrographs showing the immunofluorescent staining of multidrug resistance protein 1 (MRP1). Row E is a set of photomicrographs showing immunoglobulin G control staining for sheep, mouse, and rabbit antisera. All of these photos were taken on Day 18. The percentage of positive cells and standard deviation for two markers are listed in the table below.

| Substrate | ALB | CYP3A |
| --- | --- | --- |
| MG | 89.2% ± 7.3 | 85.5% ± 8.1 |
| LN-521 | 89.2% ± 6.0 | 90.8% ± 9.9 |
| LN-511 | 89.7% ± 5.5 | 89.5% ± 5.5 |

Figure 17:
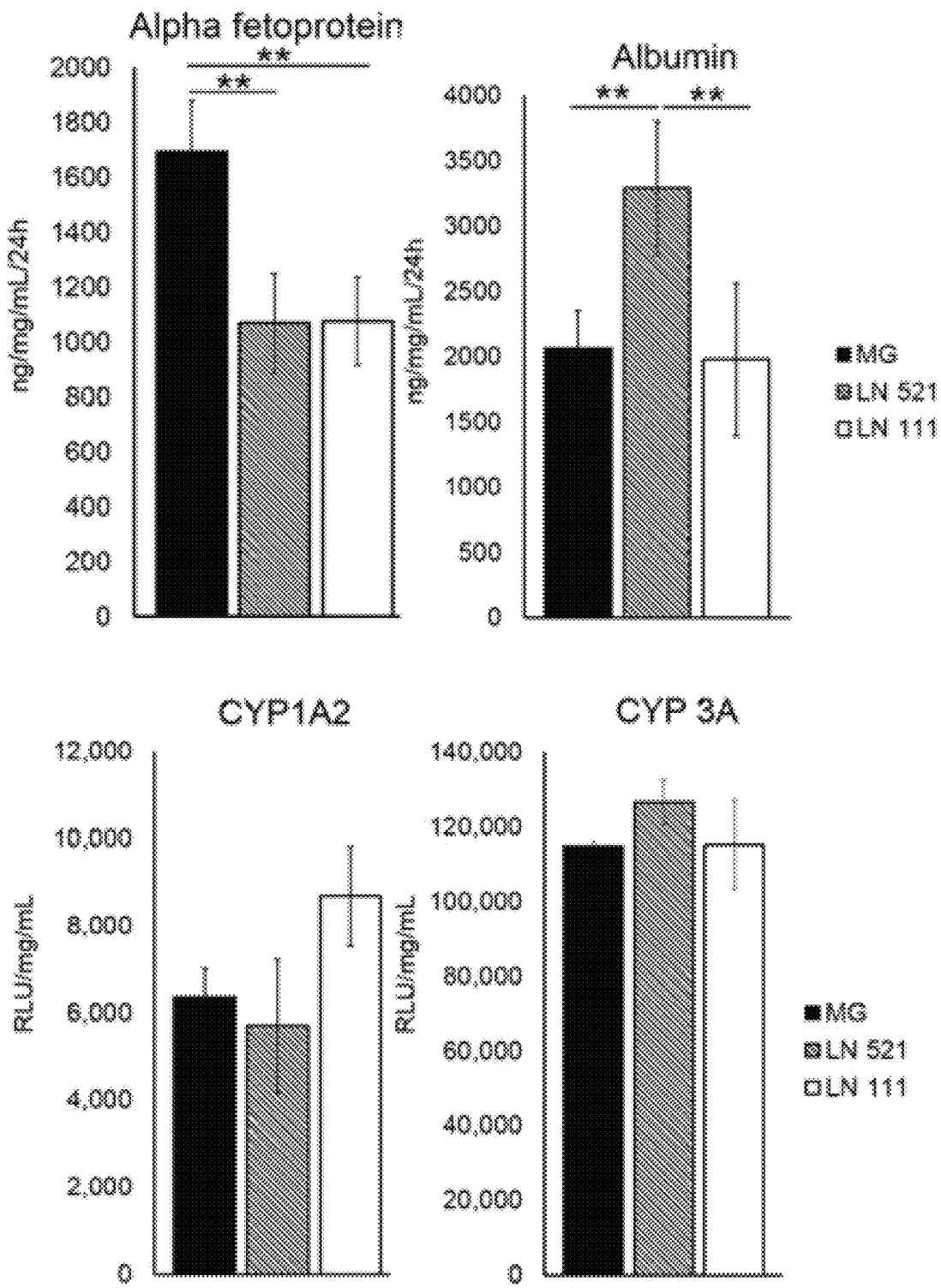
FIG. 17 is a set of four bar graphs of alpha fetoprotein, albumin, CYP1A2, and CYP3A expression during differentiation on the three different substrates of FIG. 16. For each graph, the dark bar is MG; the dashed bar is LN 521, and the white bar is LN 111. The y-axis for the alpha fetoprotein and albumin graphs is ng/mg/mL/24 hours. The y-axis for the CYP1A2 and CYP3A graphs is RLU/mg/ml. Double asterisk (**) indicates p<0.01 as measured by one-way ANOVA with Tukey post-hoc test.

FIG. 17 is a set of four bar graphs. The first row of two graphs shows hepatocyte protein secretion for alpha fetoprotein and albumin as analyzed by ELISA on day 18 of differentiation (n=3). A significant reduction in alpha fetoprotein (AFP) was observed on both LN 521 (p=2.01091E-06) and LN 111 (p=1.20688E-06). Albumin was significantly increased on LN 521 (p=1.23378E-05). The second row of two graphs show the metabolic function of CYP p450 activity on day 18 for CYP1A2 and CYP3A activity. No significant differences were observed across the three matrices.

Looking at both Example 4 and Example 5, the MAN11 and MAN12 cells differentiated efficiently on all three substrates, with the majority of cells (>80%) expressing albumin and CYP3A, as detected by immunostaining. The same level of cellular organisation was also demonstrated across the three substrates, though morphologically the cells were more defined on the laminin-containing substrates and displayed distinct hexagonal morphology. Furthermore, HLCs on the LN-521 and the LN-111 substrates displayed networks of MRP1 staining; indicating these cell populations were more polarised. Of note, H9 derived hepatocytes displayed a closer metabolic profile to primary hepatocytes than did MAN11 and MAN12 derived hepatocytes. However, both the LN-512 and the LN-111 substrates improved metabolic activity of MAN12 derived hepatocytes and significantly reduced foetal protein secretion in MAN11 derived hepatocytes, demonstrating significant progress.

Example 6

Differentiation of Pluripotent Stem Cells Towards Hepatocytes.

Cultured hESCs on pure laminin-521 coated wells were dissociated into single cells and resuspended into ROCK inhibitor supplemented mTeSR1. To make random size spheroids, 2 ml of 1×10$^6$ cell suspension was transferred into poly-hydroxyethyl methyl methacrylate (poly-HEMA)-coated 6-well plates and incubated under static conditions overnight (FIG. 18A). Coating the plate with poly-HEMA creates an ultra-low/non-adherent surface which forces self-aggregation of cells and formation of spheroids in suspension culture. In order to make uniform size spheroids, 190 microliters (p1) of 1×10$^6$, 2×10$^6$ and 4×10$^6$/ml cell suspension was added into preformed agarose microplates and incubated overnight to form spheroids with 50 µm to 100 µm diameter (FIG. 18B), 100 µm to 150 µm diameter (FIG. 18C), and 150 µm to 200 µm diameter (FIG. 18D), respectively. Similar to suspension culture, agarose mold provides a non-adherent surface which forces self-aggregation of cells in individual wells, however, the size of spheroids can be controlled by changing the seeding density. FIG. 18E compares the size ranges. Twenty four hours post replating, differentiation was initiated using a serum free stepwise procedure to derive hepatocyte-like cells from H9 and Man12 cell lines.

Gene Expression Analysis

To analyse gene expression, spheroids were collected at the denoted time points and mRNA were extracted. Both procedures delivered cell populations from H9 (research grade line) and Man12 (GMP grade line) that transited from pluripotency, through definitive endoderm, to hepatoblast-like cells and subsequently hepatocytes as demonstrated by quantitative PCR. FOXA2 expression was detected from days 3-18 (FIG. 19A). High level expression of HNF4A was detected at Day 8 with peak and declined as the cells matured in culture (FIG. 19B). Expression of alpha fetoprotein (AFP) was upregulated at Day 8 of differentiation with peak of expression at Day 18 (FIG. 19C). Low levels of albumin (ALB) were detected at Day 8 followed by a significant increase at Day 18 (FIG. 19D).

Maturation of Human Embryonic Stem Cell Derived Hepatospheres

Figures 20A, 20B:
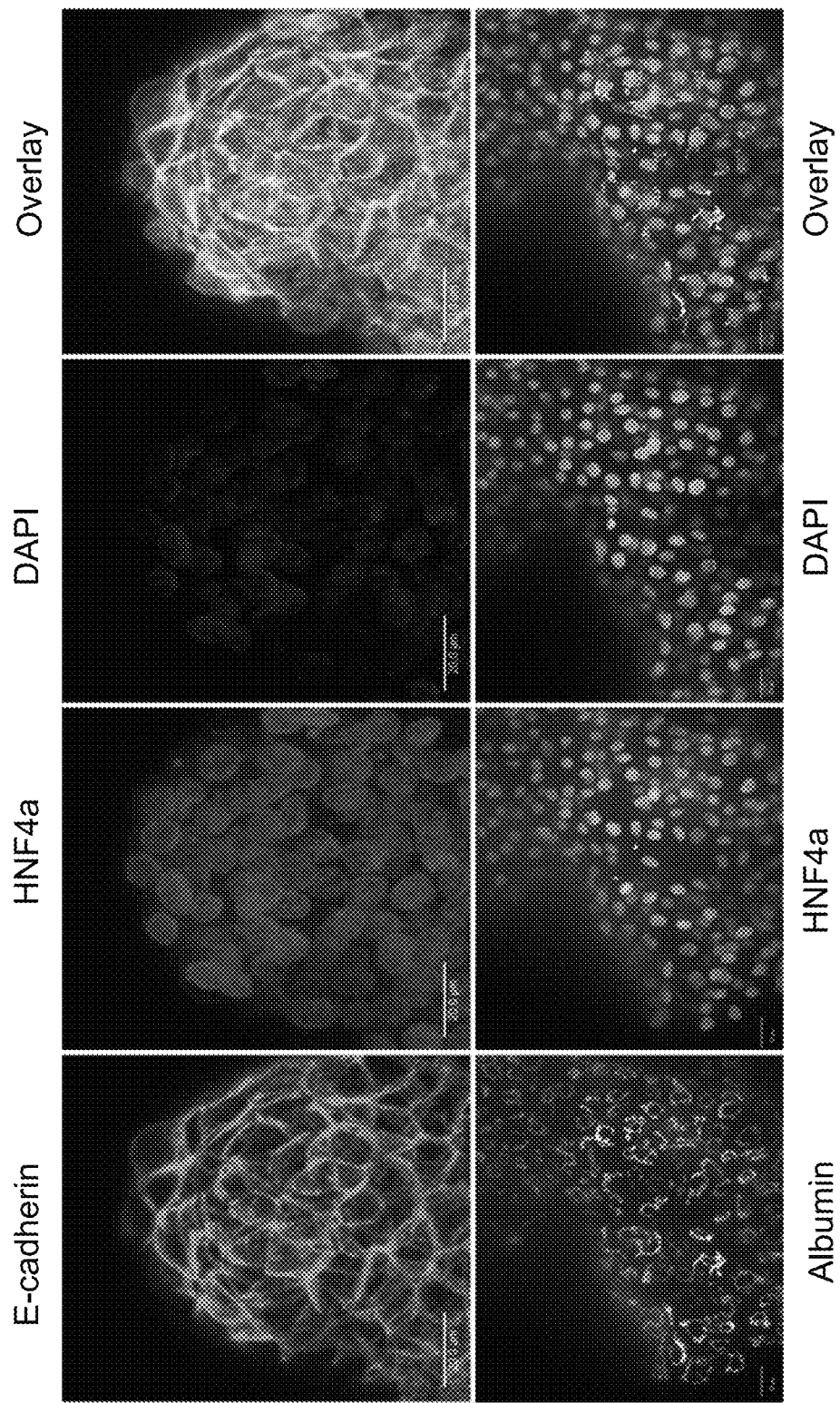
FIG. 20A is a set of four immunostains done on day 18. The leftmost stain is e-cadherin. The left center stain is HNF4a. The right center stain is DAPI. The rightmost stain is an overlay of the other three stains. The line at the bottom left of each stain indicates 20 μm.
FIG. 20B is a set of four immunostains done on day 30. The leftmost stain is albumin. The left center stain is HNF4a. The right center stain is DAPI. The rightmost stain is an overlay of the other three stains. The line at the bottom left of each stain indicates 20 μm.
Figure 21:
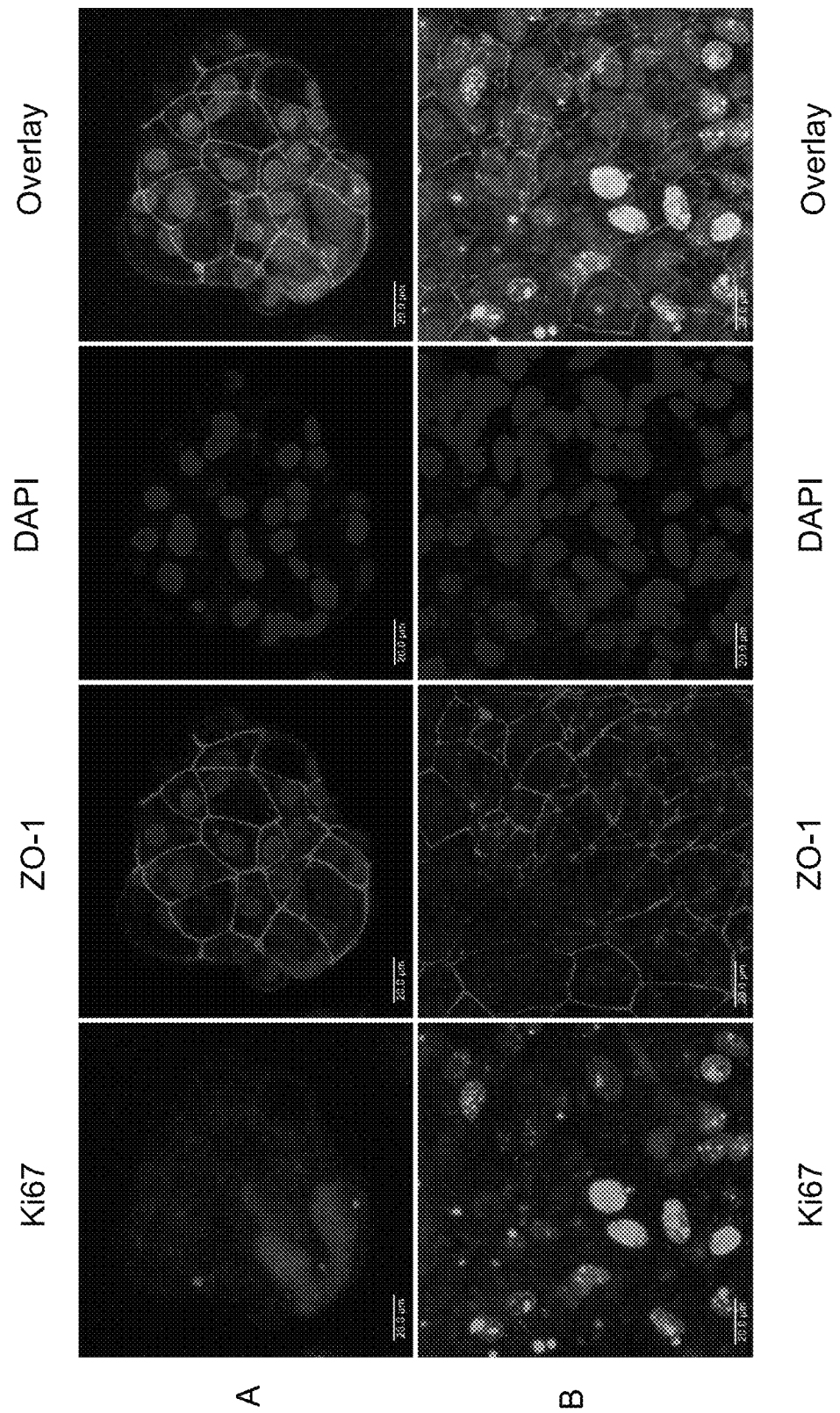
FIG. 21 is a set of eight immunostains, arranged in a row A and a row B with four stains each, all made on day 18. Row A was small hepatospheres, and Row B was large hepatospheres. The leftmost column is Ki67. The left center column is ZO-1. The right center column is DAPI. The rightmost column is an overlay of the other three columns. The line at the bottom left of each stain indicates 20 μm.
Figure 22A:
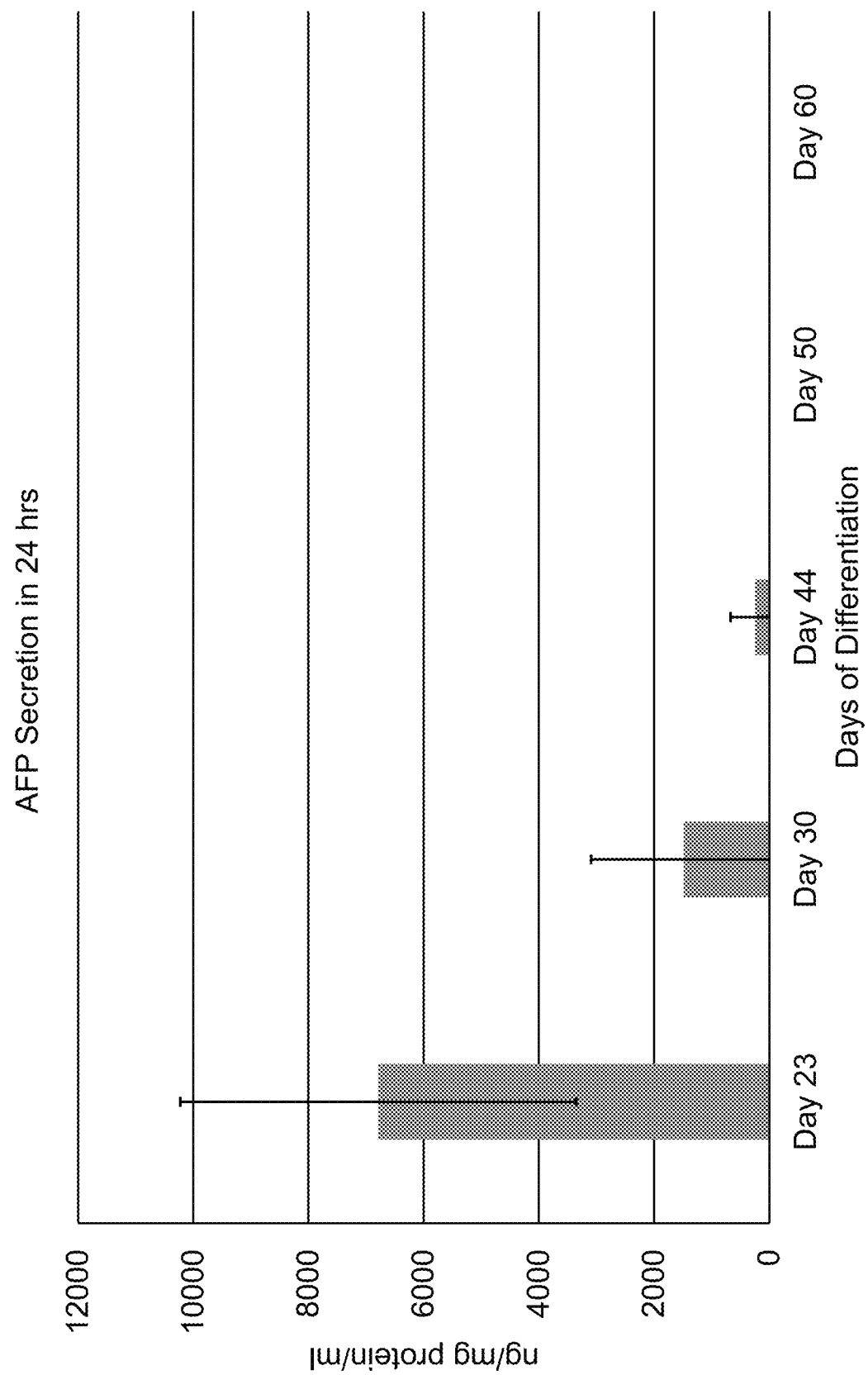
FIG. 22A is a graph showing secretion of AFP over time by hepatospheres. The y-axis is ng/mg protein/ml, and runs from 0 to 12,000 at intervals of 2,000. The x-axis is, running from left to right, day 23, day 30, day 44, and day 50.
Figure 22B:
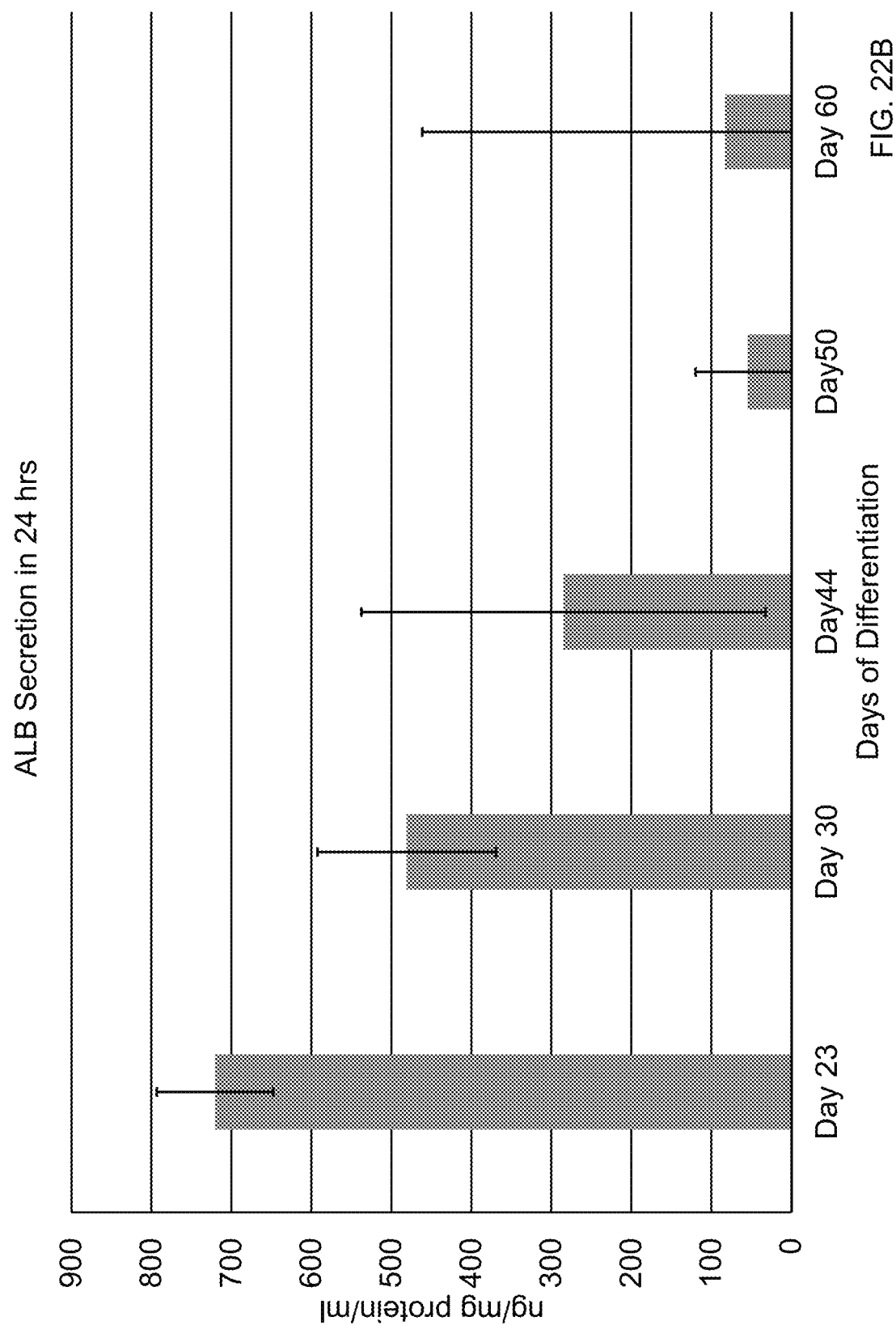
FIG. 22B is a graph showing secretion of ALB over time by hepatospheres. The y-axis is ng/mg protein/ml, and runs from 0 to 900 at intervals of 100. The x-axis is, running from left to right, day 23, day 30, day 44, and day 50.

In order to assess maturation of 3D hepatospheres, expression of hepatic markers such as hepatic nuclear factor 4A (HNF4A), and E-cadherin (Ecad) were stained for at day 18 (FIG. 20A). This was followed by immunostaining at Day 30 for mature hepatocyte markers albumin (Green) and HNF4a (orange) in FIG. 20B. ZO-1 is an important marker of cell polarity, and cell-cell contact was detected in large and small hepatospheres (FIG. 21). Notably, a lower number of cells expressing Ki67, a marker of cell proliferation, were observed in smaller hepatospheres in comparison to larger hepatospheres, (FIG. 21). To evaluate the level of liver-specific proteins secreted, AFP and ALB levels were measured by ELISA. The results indicated that AFP production was reduced by further maturation of hepatospheres and fell below detection limit by day 44 of differentiation while ALB production was continued up until day 50 (FIG. 22A and FIG. 22B).

Human Embryonic Stem Cell Derived Hepatocyte Metabolic Function

Figure 23D:
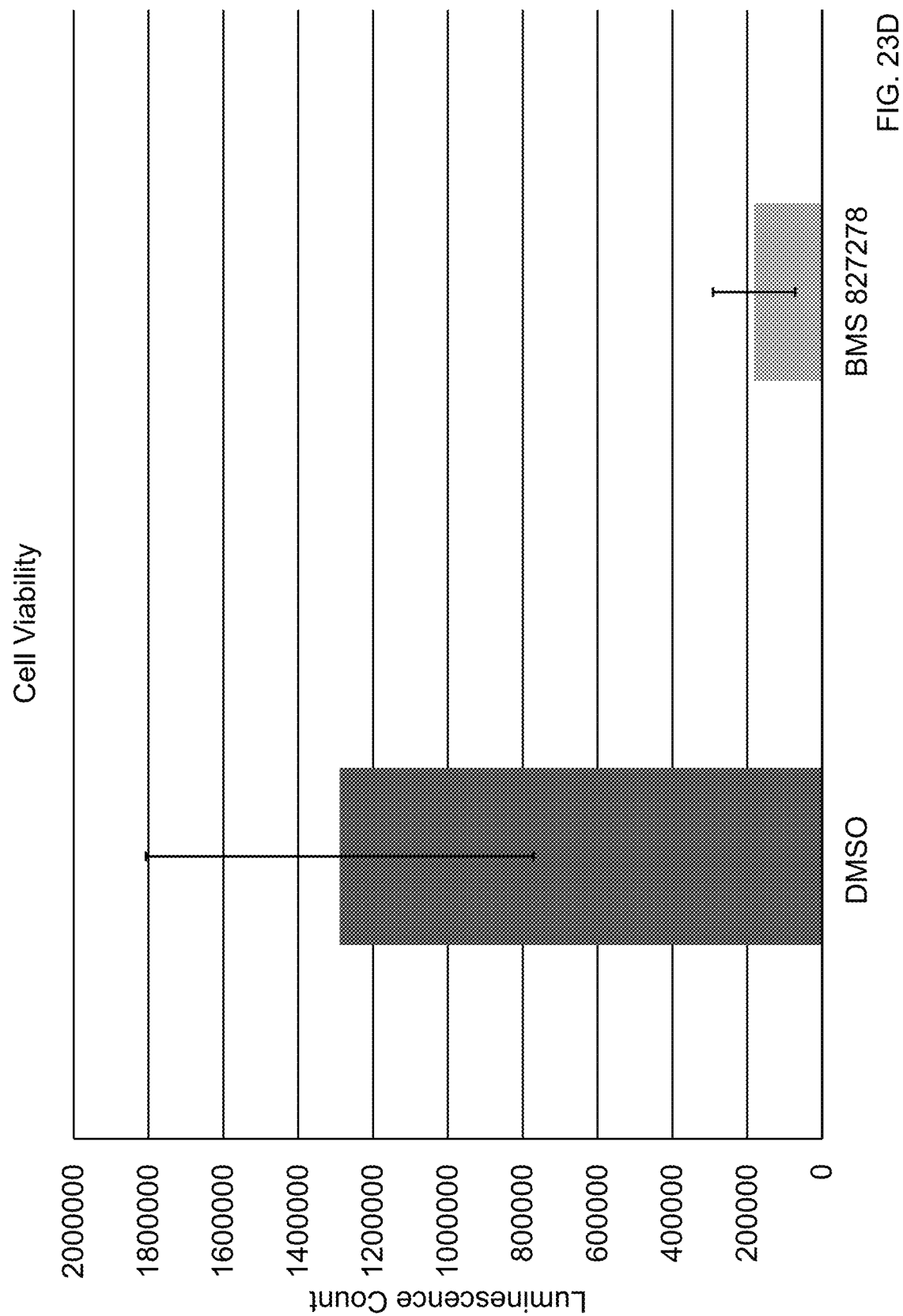
FIG. 23D is a bar graph showing CYP2D6 metabolic function. The left bar is DMSO, and the right bar is BMS-827278. The y-axis is luminescence count, and runs from 0 to 1,600,000 at intervals of 200,000. A reduction in cell viability for BMS-827278 is proportional to enzyme activity.

In order to assess metabolic competence of human stem cell derived hepatopheres, cytochrome P450 expression was examined using antisera. CYP3A and CY2D6 expression were detected throughout the 3D hepatospheres (FIG. 23A and FIG. 23B). In addition, P450 functionality of hepatospheres were assessed. CYP3A function was respectable and maintained in culture for at least 33 days (FIG. 23C). Additionally, Cyp2D6 metabolic function was measured using a pharmaceutical compound known as BMS-827278. This compound is metabolically activated to a toxic endpoint and therefore a reduction in cell viability (orange bar) is proportional to enzyme activity (FIG. 23D).

Human Embryonic Stem Cell Derived Hepatocyte Function In Vivo

In order to assess the competence of two-dimensional (2D) and three-dimensional (3D) stem cell derived hepatocytes to support murine liver function, the partial hepatectomy model of reduced liver function was employed. 2 million 2D or 3D hepatocytes were transplanted intra portally or intra peritoneally respectively. For the 2D cells, 48 hours after transplant a 30% partial hepatectomy was carried out. For the 3D cells, cells were transplanted into the peritoneum at the same time as performing the hepatectomy. 7 days post partial hepatectomy mouse body weight was recorded. Body weight was significantly increased in both transplant groups when compared to the vehicle only control. The control was about 91% initial body weight, while the 2D group was about 95% initial body weight, and the 3D group was about 100% initial body weight.

We been developed to a 3D system to derive functional hepatocyte-like cells with stable phenotype. Both protocols resulted in efficient production of spheroids from hPSC cultured and maintained on laminin 521, however, control over the size of formed spheroids was challenging using suspension methodology. In contrast, the size of spheroids can be controlled using microplate platform with small variation in spheroid size.

3D hepatospheres showed more stable phenotype and prolonged metabolic functionality up to day 60 of differentiation Furthermore, hepatocyte-like cells derived under 3D conditions displayed highly polarized structures evident by expression of e-cadherin and ZO-1. Notably, a lower number of proliferating cells was observed in small hepatospheres at day 18, while a higher number was detected in larger spheroids, indicating the importance of size in regulation of cell behaviour. Importantly, 3D hepatospheres demonstrated suitable function in vitro and also supported mammalian liver function in vivo.

The present disclosure has been described with reference to exemplary embodiments. Obviously, modifications and alterations will occur to others upon reading and understanding the preceding detailed description. It is intended that the present disclosure be construed as including all such modifications and alterations insofar that they come within the scope of the appended claims or the equivalents thereof.

The invention claimed is:

1. A method for producing hepatocytes, comprising:
plating pluripotent human stem cells on a cell culture substrate comprising (i) a first laminin which is laminin-521 and (ii) a second laminin selected from the group consisting of laminin-111 and laminin-221, wherein the laminin-521 and the second laminin are each an intact protein; and
culturing the pluripotent human stem cells on the cell culture substrate to obtain the hepatocytes, wherein the culturing is performed by:
culturing the cells in an endoderm differentiation medium containing activin A, Wnt3a, and hepatocyte growth factor;
culturing the cells in a hepatic specification medium containing a serum replacement and dimethyl sulfoxide;
culturing the cells in a hepatic differentiation medium; and
culturing the cells in a hepatic maturation medium containing hepatocyte growth factor (HGF).

2. The method of claim 1, wherein the weight ratio of the laminin-521 to the second laminin is from about 1:4 to about 1:1.

3. The method of claim 1, wherein the cells are cultured in the endoderm differentiation medium for a period of about 60 hours to about 84 hours.

4. The method of claim 1, wherein the cells are cultured in the hepatic specification medium for a period of about 84 hours to about 108 hours.

5. The method of claim 1, wherein the cells are cultured in the hepatic differentiation medium for a period of about 108 hours to about 132 hours.

6. The method of claim 1, wherein the cells are cultured in the hepatocyte maturation medium for a period of about 84 hours to about 108 hours.

7. The method of claim 1, wherein the activin A is present in the endoderm differentiation medium in an amount of about 50 ng/mL to about 150 ng/mL.

8. The method of claim 1, wherein the Wnt3a is present in the endoderm differentiation medium in an amount of about 20 ng/mL to about 100 ng/mL.

9. The method of claim 1, wherein the endoderm differentiation medium further includes RPMI 1640.

10. The method of claim 1, wherein the hepatic specification medium comprises 20% of the Serum Replacement, 1% non-essential amino acids, 0.33 mM beta-mercaptoethanol, and 1% of the dimethyl sulfoxide.

11. The method of claim 1, wherein the hepatocyte growth factor is present in the hepatic maturation medium in an amount of about 5 ng/mL to about 20 ng/mL.

12. The method of claim 1, wherein oncostatin m is present in the hepatic differentiation medium in an amount of about 10 ng/mL to about 30 ng/mL.

13. The method of claim 1, wherein the resulting hepatocytes exhibit CYP1A2 activity of at least 600,000 RLU/mg/mL or CYP3A activity of at least 800,000 RLU/mg/mL.

14. The method of claim 1, wherein the second laminin is laminin-221.

15. The method of claim 1, wherein the cell culture substrate further comprises a cadherin.

16. The method of claim 15, wherein the weight ratio of (the first laminin+the second laminin) to the cadherin is from about 5:1 to about 15:1.

17. The method of claim 1, wherein the cell culture substrate does not contain any differentiation inhibitors, feeder cells, differentiation inductors, or apoptosis inhibitors.

18. The method of claim 1, wherein the pluripotent human stem cells have a three-dimensional structure prior to culturing.

19. A method for producing hepatocytes, comprising:
plating pluripotent human stem cells on a cell culture substrate comprising (i) a first laminin which is laminin-521 and (ii) a second laminin selected from the group consisting of laminin-111 and laminin-221, wherein the laminin-521 and the second laminin are each an intact protein; and
culturing the pluripotent human stem cells on the cell culture substrate to obtain the hepatocytes, wherein the culturing is performed by:
culturing the cells in an endoderm differentiation medium comprising activin A, Wnt3a, and hepatocyte growth factor;
culturing the cells in a hepatic specification medium containing a serum replacement and dimethyl sulfoxide;
culturing the cells in a hepatic differentiation medium containing insulin, dexamethasone, oncostatin M, and basic fibroblast growth factor; and
culturing the cells in a hepatic maturation medium containing insulin, lithocholic acid, vitamin K, hepatocyte growth factor, and dexamethasone.

20. The method according to claim 19, wherein the resulting hepatocytes exhibit CYP1A2 activity of at least 600,000 RLU/mg/mL or CYP3A activity of at least 800,000 RLU/mg/mL.

* * * * *